United States Patent [19]

Neishi et al.

[11] Patent Number: 5,024,912

[45] Date of Patent: Jun. 18, 1991

[54] 5H-DIBENZO(A,D) CYCLOHEPTANYLIDENE DERIVATIVE AND 5H-DIBENZO (A,D) CYCLOHEPTENYLIDENE DERIVATIVE, AND ELECTROPHOTOGRAPHIC PHOTOSENSITIVE MEMBER USING THE SAME

[75] Inventors: Toshie Neishi, Kawasaki; Toshihiro Kikuchi, Yokohama; Takao Takiguchi, Tokyo; Koichi Suzuki, Kawasaki; Masakazu Matsumoto, Yokohama, all of Japan

[73] Assignee: Canon Kabushiki Kaisha, Tokyo, Japan

[21] Appl. No.: 351,304

[22] Filed: May 10, 1989

Related U.S. Application Data

[63] Continuation of Ser. No. 93,251, Sep. 4, 1987, abandoned.

[30] Foreign Application Priority Data

Sep. 10, 1986 [JP] Japan ............................. 61-213320
Aug. 25, 1987 [JP] Japan ............................. 62-212152

[51] Int. Cl.⁵ .................. G03G 5/06; G03G 5/09; C07C 211/31
[52] U.S. Cl. ......................... 430/59; 430/58; 430/72; 430/73; 430/74; 430/75; 430/76; 430/78; 546/143; 546/159; 546/285; 549/68; 549/480; 564/318; 564/391
[58] Field of Search ............... 564/318, 391; 546/143, 546/159, 285; 549/68, 480; 430/58, 59, 72, 73, 74, 75, 76, 78

[56] References Cited

U.S. PATENT DOCUMENTS 3,472,869 10/1969 Humber .................. 564/338 X
3,533,786 10/1970 Looker ................... 564/308 X
4,070,373 1/1978 Winter et al. ............ 564/379 X
4,245,021 1/1981 Kazami et al. ........... 430/059 X
4,579,799 4/1986 Katagiri et al. .......... 430/074 X

OTHER PUBLICATIONS

Streitweiser, A., Murdock, J. R., Häefelinger, G., and Chang, C. J., "Acidity of Hydrocarbons XLVI. Equilibrium Ion Pair Acidities of Mono-Di-Triaryl Methanes Toward Cesium Cyclohexamide", J.A.C.S., 95:13, pp. 4248-4254 (Jun. 27, 1973).

*Primary Examiner*—Girard L. Raymond
*Attorney, Agent, or Firm*—Fitzpatrick, Cella, Harper & Scinto

[57] ABSTRACT

A 5H-dibenzo [a,d] cycloheptenylidene derivative and a 5H-dibenzo [1,d] cycloheptenylidene derivative represented by the following general formula [I]:

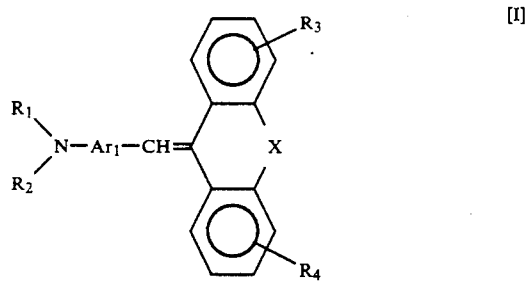

wherein X is $-CH_2-CH_2-$ or $-CH=CH-$; $R_1$ and $R_2$ are alkyl groups, aralkyl groups, aromatic groups or heterocyclic groups, $R_3$ and $R_4$ are hydrogen atoms, alkyl groups, alkoxy groups or halogen atoms; and $Ar_1$ is an aromatic group or a heterocyclic group, process for producing those derivatives, and electrophotographic photosensitive member using the same.

13 Claims, 13 Drawing Sheets

5H-DIBENZO(A,D) CYCLOHEPTANYLIDENE DERIVATIVE AND 5H-DIBENZO (A,D) CYCLOHEPTENYLIDENE DERIVATIVE, AND ELECTROPHOTOGRAPHIC PHOTOSENSITIVE MEMBER USING THE SAME

This application is a continuation of application Ser. No. 093,251 filed Sept. 4, 1987, now abandoned.

BACKGROUND OF THE INVENTION

1. Field of the Invention

This invention relates to novel 5H-dibenzo[a,d] cycloheptanylidene derivatives and 5H-dibenzy[a,d]cycloheptenylidene derivatives, a process for producing the same and an electrophotographic photosensitive member using the same.

2. Related Background Art

Heretofore, inorganic photoconductive materials such as selenium, zinc oxide, cadmium sulfide, etc. have been widely used in the electrophotographic photosensitive layer, and recently research for using organic photoconductive materials as an electrophotographic photosensitive member have been extensively made.

Basic characteristics required for the electrophotographic photosensitive member are 1) a good chargeability up to an appropriate potential in a dark place by corona discharge, etc., 2) a good charge retention in a dark place, 3) a rapid potential dischargeability by light irradiation, 4) less residual potential after the light irradiation, etc.

Electrophotographic photosensitive members using the conventional inorganic electroconductive materials such as selenium, zinc oxide, cadmium sulfide, etc. have the said basic characteristics to some extent, but still have such production problems as difficult film formability, poor flexibility, a high production cost, etc. Furthermore, inorganic photoconductive materials generally have a high toxicity, and thus it is desirable from this point of view to use an organic photosensitive member in place of the inorganic photosensitive member. Generally, organic materials have such advantages as light weight, good film formability and flexibility, low production cost, low toxicity, etc., as compared with inorganic materials.

Thus, recent research for electrophotographic photoconductive materials using organic materials, have been extensively made, and many electrophotographic photosensitive members have been proposed and practically used.

Various organic photoconductive polymers including poly-N-vinylcarbazole as a typical organic electrophotographic photosensitive material have been so far proposed, and are better in the weight, film formability, etc., than inorganic photoconductive materials, but are poorer in the sensitivity, durability, stability against changes in surrounding atmosphere, mechanical strength, etc., than the inorganic photoconductive materials and thus are practically less used.

Low molecular weight, organic photoconductive materials such as hydrozone compounds disclosed in U.S. Pat. No. 4,150,987, triarylpyrazoline compounds disclosed in U.S. Pat. No. 3,837,851, and 9-styrylanthracene compounds disclosed in Japanese Patent Publications Kokai (Laid-open) Nos. 94828/1976 and 94829/1976, etc. have been proposed. These low molecular weight, organic photoconductive materials can overcome the disadvantage of poor film formability as a problem in the field of organic photoconductive polymers by properly selecting a binder to be used, but still are not satisfactory in their sensitivity.

Recently, a laminated structure type, in which the photosensitive layer is functionally divided into a charge generation layer and a charge transport layer, has been proposed. An electrophotographic photosensitive member using a photosensitive layer of such a laminated structure type has improvements in the sensitivity to visible light, charge retention, surface strength, etc. Such electrophotographic photosensitive members as above are disclosed, for example, in U.S. Pat. Nos. 3,837,851, 3,871,882 and 4,245,021; British Patent No. 2,121,789 [Japanese Patent Application Kokai (Laid-open) No. 198043/1976], Japanese Patent Application Kokai (Laid-open) No. 161247/1980, etc.

However, the electrophotographic photosensitive members using the conventional low molecular weight, organic photoconductive material in the charge transport layer are not always satisfactory in sensitivity and characteristics, and have a large fluctuation in the light portion potential and the dark portion potential when subjected to repeated charging and light exposure and thus still have points to be improved.

As a result of extensive studies of organic photoconductive materials for electrophotographic photosensitive members, the present inventors have synthesized novel 5H-dibenzo[a,d]cycloheptanylidene derivatives and 5H-dibenzo[a,d]cycloheptenylidene derivatives, each having a 7-membered ring structure, and have found that these compounds are very useful as the organic photoconductive materials.

SUMMARY OF THE INVENTION

An object of the present invention is to provide novel compounds free from the said problems or disadvantages of the photoconductive materials.

Another object of the present invention is to provide novel organic photoconductive materials.

Other object of the present invention is to provide novel charge transfer materials in a photosensitive layer of laminated structure type in which the photosensitive layer is functionally separated into a charge generation layer and a charge transport layer.

The present invention provides a 5H-dibenzo[a,d]cycloheptanylidene derivative and a 5H-dibenzo[a,d]cycloheptenylidene derivative, a process for producing the same and an electrophotographic photosensitive member using the same.

DETAILED DESCRIPTION OF THE INVENTION

Figure 1:
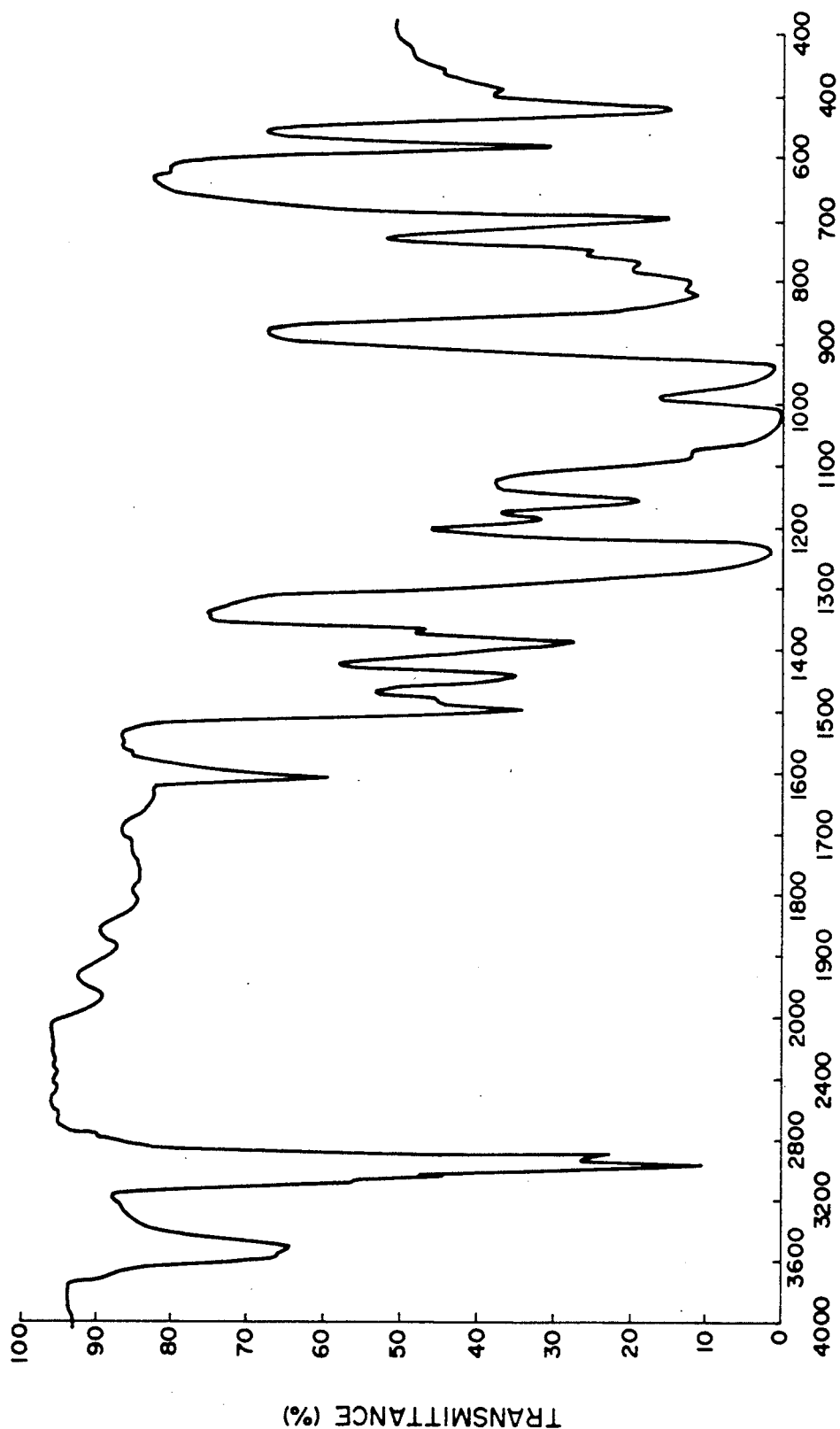
FIGS. 1 and 2 are infrared absorption spectral diagrams according to a neat method.

The present invention provides a 5H-dibenzo[a,d]cycloheptanylidene derivative and a 5H-dibenzo[a,d]cycloheptenylidene derivative represented by the following general formula [I]:

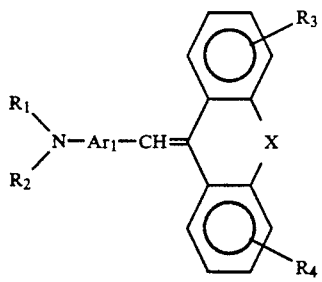

[I]

wherein X is —CH₂CH₂— or —CH=CH—; R₁ and R₂ are alkyl groups, aralkyl groups, aromatic groups or heterocyclic groups, where specifically the alkyl groups include methyl, ethyl, propyl, etc., the aralkyl groups include benzyl, phenethyl, naphthylmethyl, etc.; the aromatic groups include phenyl, naphthyl, etc., and the heterocyclic groups include pyridyl, quinolyl, thienyl, furyl, etc., and the alkyl groups, aralkyl groups, aromatic groups and heterocyclic groups may contain a substituent, where the substituent includes, for example, an alkyl group such as methyl, ethyl, propyl, etc., an alkoxy group such as methoxy, ethoxy, propoxy, etc., a halogen atom such as fluorine, chlorine, bromine, etc., a nitro group, etc.; R₃ and R₄ are hydrogen atom, alkyl groups, alkoxy groups and halogen atom, where the alkyl groups, alkoxy groups and halogen atom are the same as specifically mentioned above, and the alkyl groups and alkoxy groups may contain a substituent as mentioned above; Ar₁ is an aromatic group or a heterocyclic group, where the aromatic group and heterocyclic group are the same as specifically mentioned above, and the aromatic group and heterocyclic group may contain a substituent, for example, the same alkyl group, alkoxy group, halogen atom, nitro group, etc. as mentioned above.

The present invention further provides a process for producing a 5H-dibenzo[a,d]cycloheptanylidene derivative and a 5H-dibenzo[a,d]cycloheptenylidene derivative, represented by the following general formula [I]:

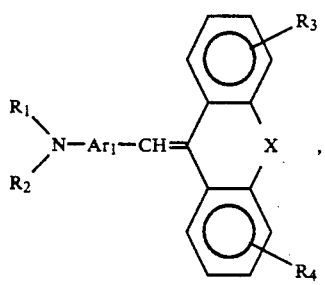

[I]

characterized by reacting an amino derivative represented by the following general formula [IV]:

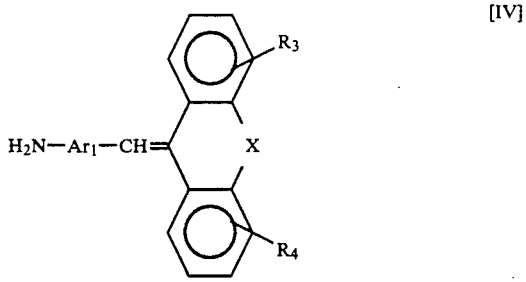

[IV]

with a halogen compound represented by the following general formula [V]:

R₆—Y [V]

wherein X is —CH₂CH₂— or —CH=CH—; R₁, R₂, R₃, R₄ and Ar₁ have the same meanings as defined above; R₆ is an alkyl group, an aralkyl group, an aromatic group or a heterocyclic group, where specifically the alkyl group includes methyl, ethyl, propyl etc., the aralkyl group includes benzyl, phenethyl, naphthyl methyl, etc., the aromatic group includes phenyl naphthyl, etc., and the heterocyclic group includes pyridyl, quinolyl, furyl, etc., and the alkyl group, aralkyl group, aromatic group and heterocyclic group may contain a substituent, where the substituent is, for example, an alkyl group such as methyl, ethyl, propyl, etc., an alkoxy group such as methoxy, ethoxy, propoxy, etc., a halogen atom such as fluorine, chlorine, bromine, etc., and a nitro group; and Y is chlorine, bromine or iodine.

The present invention furthermore provides an electrophotographic photosensitive member characterized by comprising a layer containing a compound represented by the following general formula [I]:

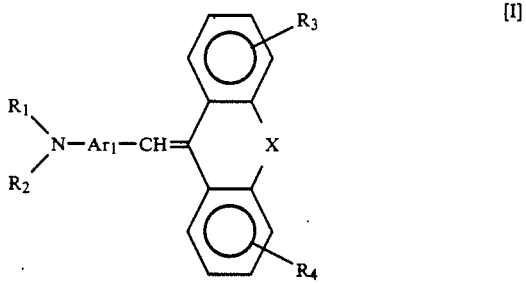

[I]

wherein X is —CH₂CH₂— or —CH=CH—; R₁ and R₂ are alkyl groups, aralkyl groups, aromatic groups or heterocyclic groups, where specifically the alkyl groups include methyl, ethyl, propyl, etc., the aralkyl groups include benzyl, phenethyl, naphthylmethyl, etc., the aromatic groups include phenyl, naphthyl, etc., and the heterocyclic groups include pyridyl, quinolyl, thienyl, furyl, etc., and the alkyl groups, aralkyl groups, aromatic groups and heterocyclic groups may contain a substituent, where the substituent includes, for example, an alkyl group such as methyl, ethyl, propyl, etc., an alkoxy group such as methoxy, ethoxy, propoxy, etc., a halogen atom such as fluorine, chlorine, bromine, etc., a nitro group, etc.; R₃ and R₄ are hydrogen atoms, alkyl groups, alkoxy groups or halogen atoms, where the alkyl groups and the alkoxy groups are the same as specifically mentioned above, and may contain such a substituent as mentioned above; Ar₁ is an aromatic group or a heterocyclic group, where specifically the aromatic group includes phenyl, naphthyl, etc., and the heterocyclic group includes pyridyl, quinolyl, thienyl, furyl, etc., and the aromatic group and heterocyclic group may contain a substituent, and further the substituent for Ar₁ includes, for example, an alkyl group such as methyl, ethyl, propyl, etc., an alkoxy group such as methoxy, ethoxy, propoxy, etc., a halogen atom such as fluorine, chlorine, bromine, etc., a nitro group, etc.

The amino derivative represented by the general formula [IV] for use in the present invention can be synthesized generally according to the following reaction route:

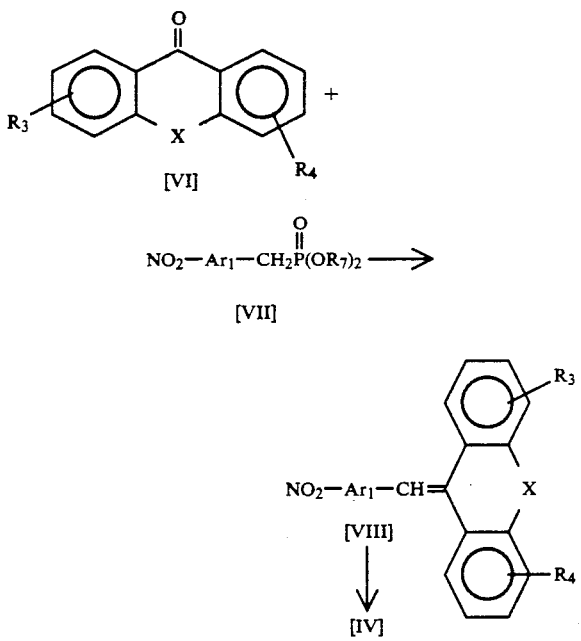

wherein X, R₃, R₄ and Ar₁ have the same meanings as defined above and R₇ is an alkyl group having 1 to 4 carbon atoms.

That is, a 5H-dibenzo[a,d]cycloheptane-5-on derivative or a 5H-dibenzo[a,d]cycloheptene-5-on derivative [VI] is allowed to react with a dialkyl phosphonate derivative [VII] in the presence of a basic catalyst at a temperature from room temperature to about 100° C. to obtain a nitro compound [VIII].

The basic catalyst includes caustic soda, caustic potash, sodium amide, sodium hydride, methyl lithium, n-butyl lithium; and alcoholates such as sodium methylate, potassium-t-butoxide, etc. As a reaction solvent, methanol, ethanol, butanol, 2-methoxyethanol, 1,2-dimethoxyethane, dioxane, tetrahydrofuran, diethyl ether, toluene, xylene, dimethyl sulfoxide, N,N-dimethyl formamide, etc. can be mentioned, among which a polar solvent such as dimethyl sulfoxide, N,N-dimethyl formamide, etc. is often preferable.

The dialkyl phosphonate derivative [VII] can be readily synthesized generally according to any of the following reaction routes:

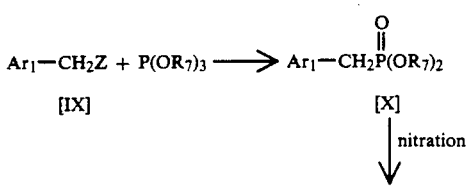

NO₂—Ar₁—CH₂Z + P(OR₇)₃ ⟶ [VII]

[XI]

wherein Ar₁ and R₇ have the same meanings as defined above, and Z is a halogen atom such as chlorine, bromine, iodine, etc.

That is, the corresponding halomethyl compound [IX] or [XI] and trialkyl phosphite are heated directly or in a solvent such as toluene, xylene, etc., to obtain a compound [X] or [VII]. In the case of compound [X], the compound [X] is further nitrated according to the ordinary method, whereby the compound [VII] can be readily obtained. As the trialkyl phosphite, those having an alkyl group having 1 to 4 carbon atoms, particularly methyl and ethyl are preferable.

The thus obtained nitro compound [VII] can be converted to an amino derivative represented by the general formula [IV] with an ordinary reducing agent, for example, iron, zinc, sodium sulfite, sulfur, sodium hydrosulfide, sodium dithionate, hydrazine, etc.

The thus obtained amino derivative represented by the general formula [IV] is allowed to react with a halogen compound represented by the general formula [V] in the presence of a basic catalyst, whereby a 5H-dibenzo[a,d]cycloheptanylidene derivative or 5H-dibenzo[a,d]cycloheptenylidene derivative represented by the general formula [I] can be obtained.

When R₆ is an alkyl group or an aralkyl group, caustic soda, caustic potash, sodium amide, sodium hydride, or an alcoholate such as sodium methylate, potassium-t-butoxide, etc. can be used as the basic catalyst. As a reaction solvent, methanol, ethanol, butanol, 2-methoxyethanol, 1,2-dimethoxyethane, dioxane, tetrahydrofuran, toluene, xylene, dimethyl sulfoxide, N,N-dimethyl formamide, etc. can be used. A wide range of reaction temperature can be selected, depending on 1) the stability of a basic catalyst against the solvent used, 2) reactivity of reaction components (compounds of general formulae [IV] and [V]), etc., and is actually from room temperature to 140° C., preferably from room temperature to about 80° C.

When R₆ is an aromatic group or a heterocyclic group on the other hand, no substantial reaction proceeds usually under the same reaction conditions as when R₆ is an alkyl group or an aralkyl group as mentioned above, and the synthesis can be made according to the following reaction.

The reaction is carried out with heating to about 100°–about 250° C., using potassium carbonate, sodium carbonate, sodium hydride, etc. as a basic catalyst and N,N-dimethyl formamide, dimethyl sulfoxide, p-cymene, o-dichlorobenzene, nitrobenzene, etc., as a reaction solvent. In some cases, the reaction may be carried out without using any solvent. A wide range of reaction temperature can be selected, depending on the reactivity of reaction components (compounds of general formulae [IV] and [V]). It is often preferable to carry out the reaction in the presence of a catalyst such as copper or copper oxide. In order to shorten the reaction time or to use a compound of poor reactivity, the reaction may be carried out at a higher temperature or under a high pressure in an autoclave, etc.

The thus obtained novel 5H-dibenzo[a,d]cycloheptanylidene derivative and 5H-dibenzo[a,d]cycloheptenylidene derivative according to the present invention can be exemplied as follows:
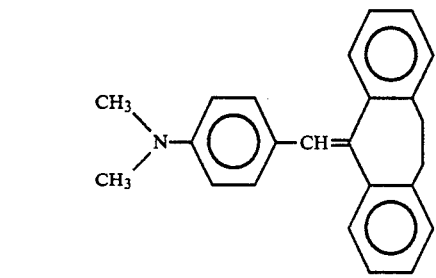 (1)
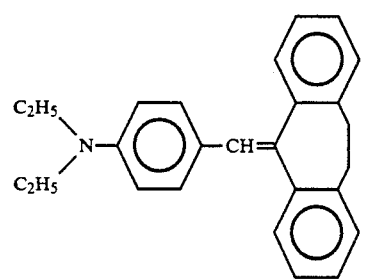 (2)
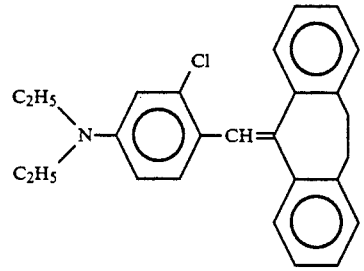 (3)
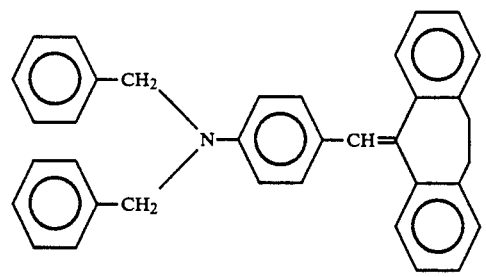 (4)
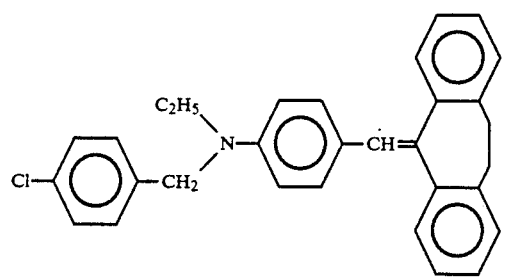 (5)
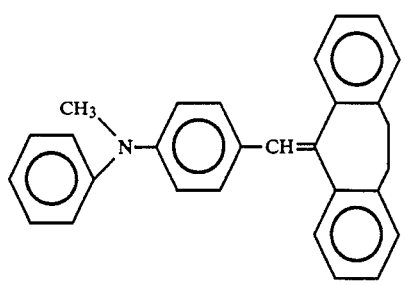 (6)
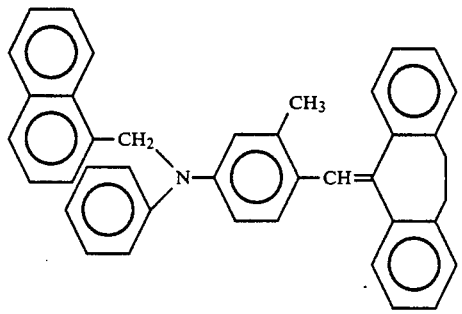 (7)
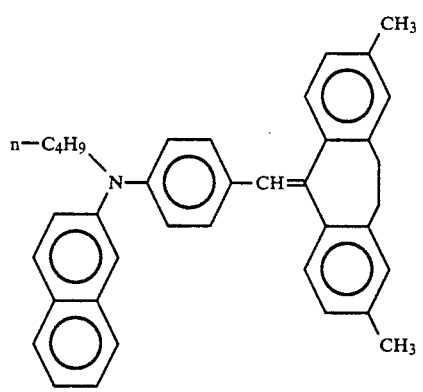 (8)
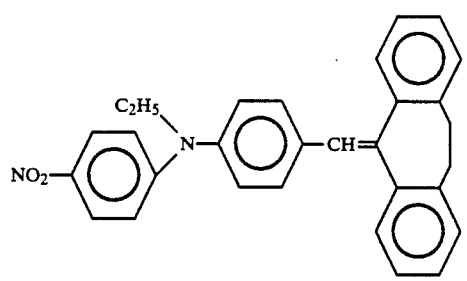 (9)
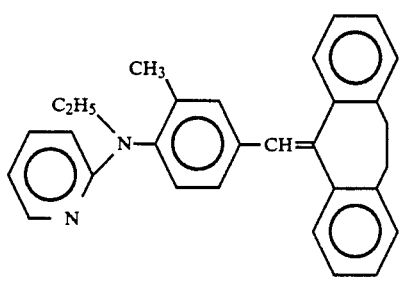 (10)

-continued
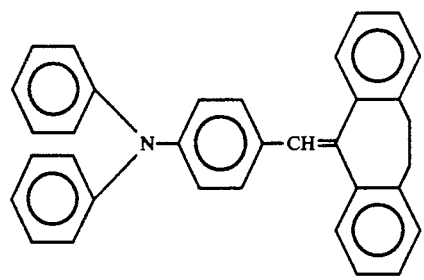 (11)
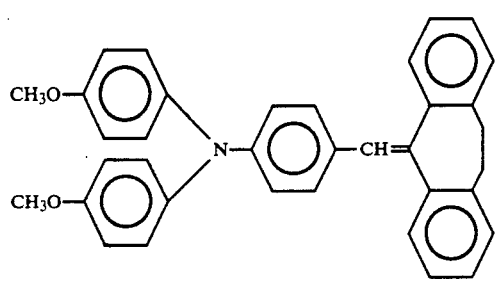 (12)
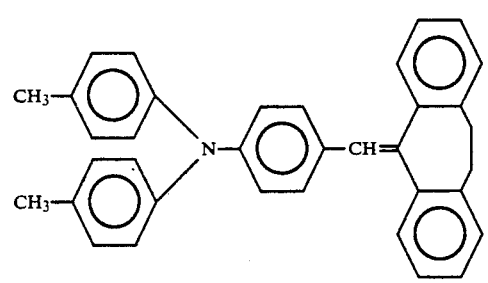 (13)
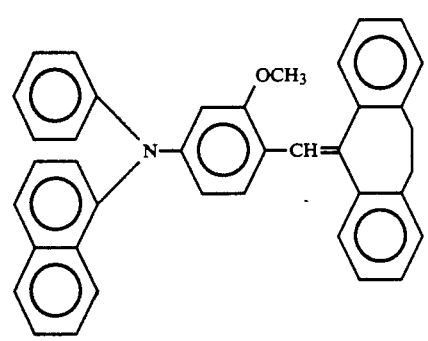 (14)
(15)
-continued
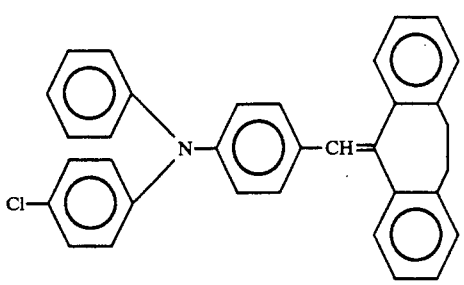 (16)
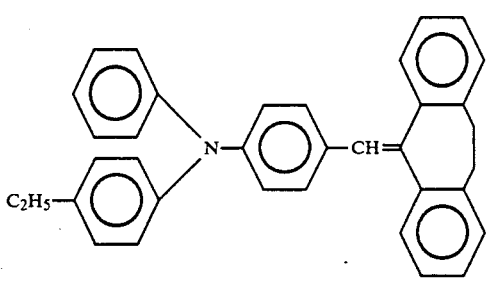 (17)
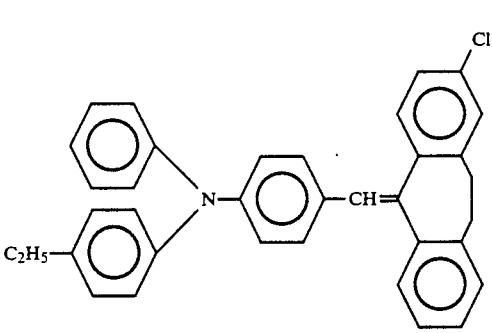 (18)
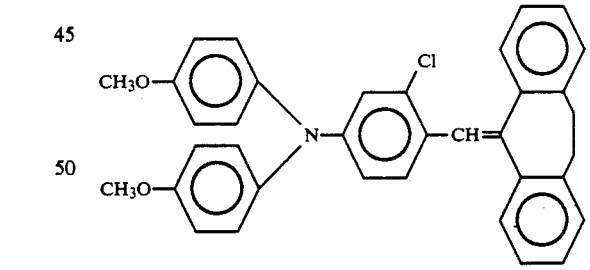 (19)
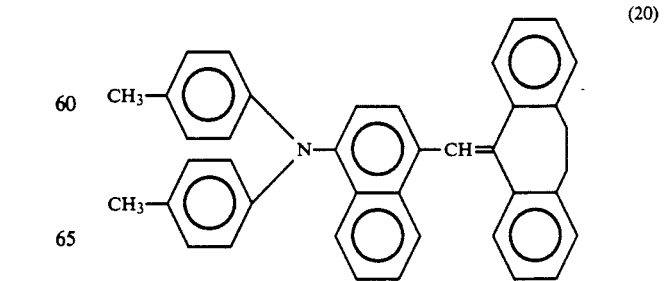 (20)

-continued
(21)
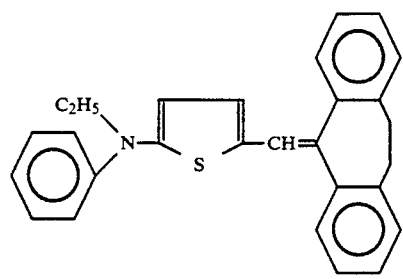
(22)
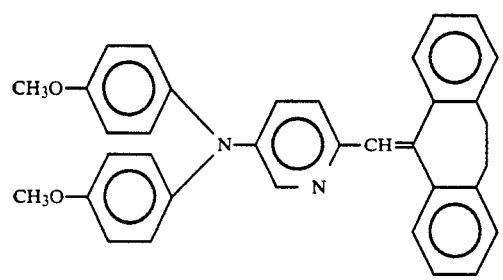
(23)
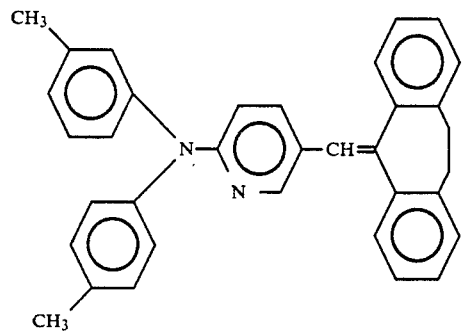
(24)
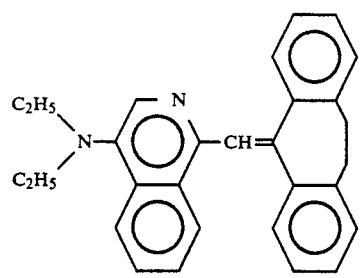
(25)
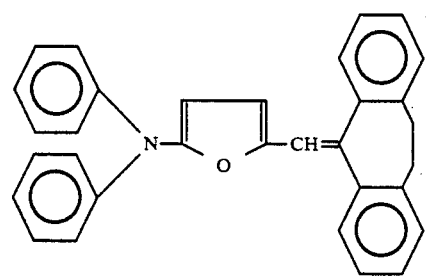
-continued
(26)
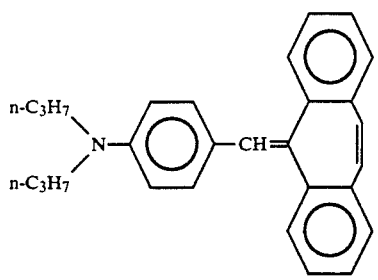
(27)
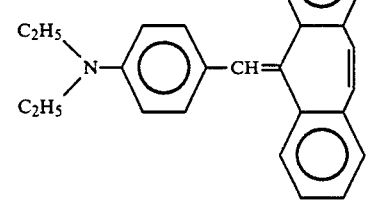
(28)
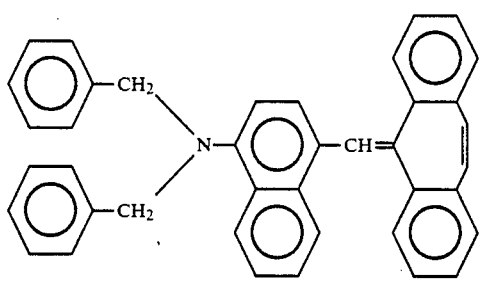
(29)
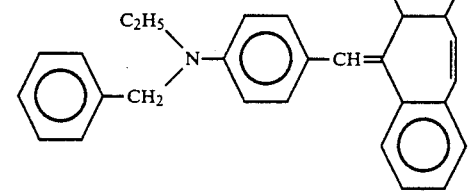
(30)
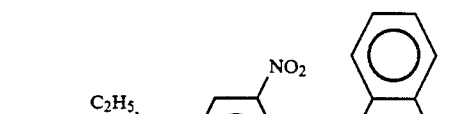
(31)

-continued

(32) (37) (33) (38) (34) (39) (35) (40) (36) (41)

-continued
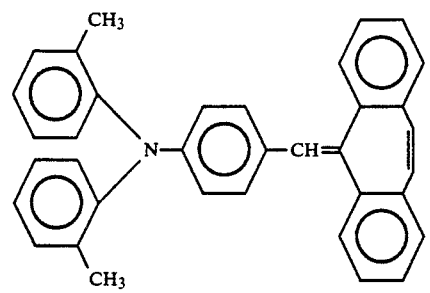
(42)
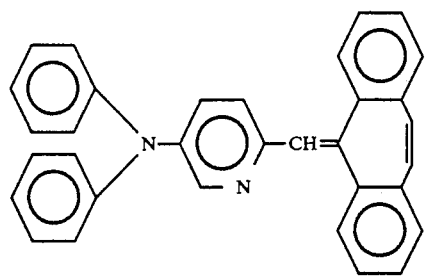
(47)
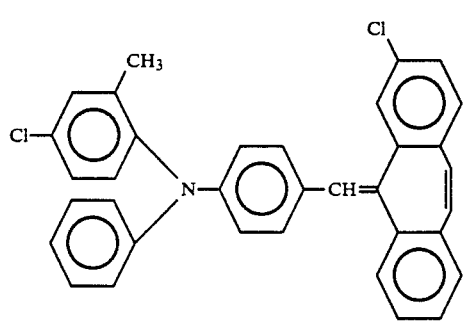
(43)
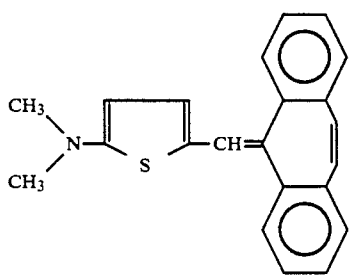
(48)
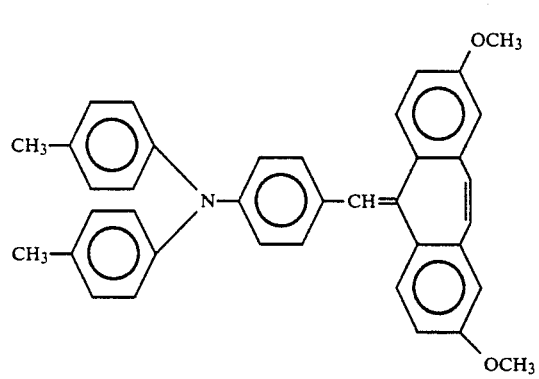
(44)
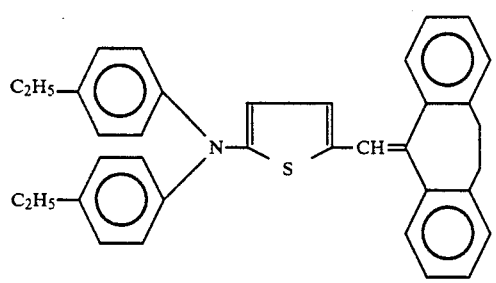
(49)
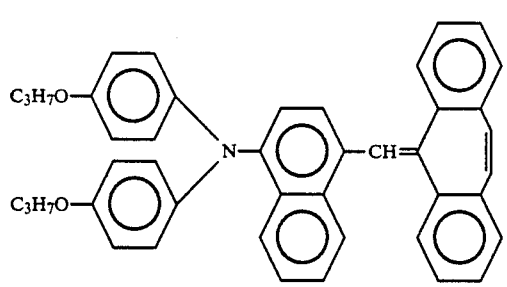
(45)
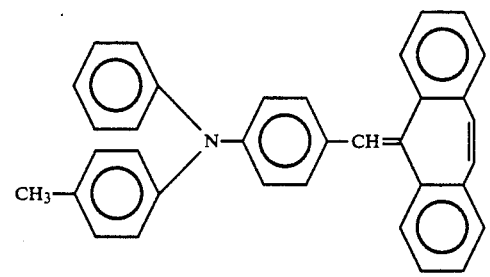
(50)
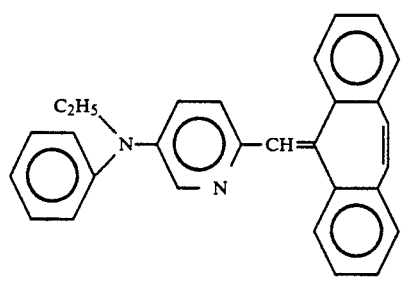
(46)
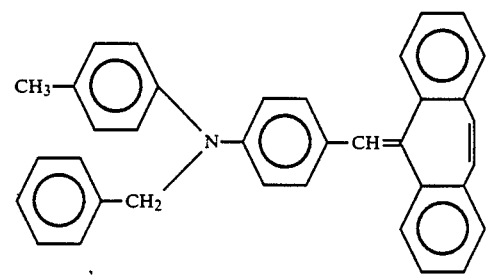
(51)
(52)

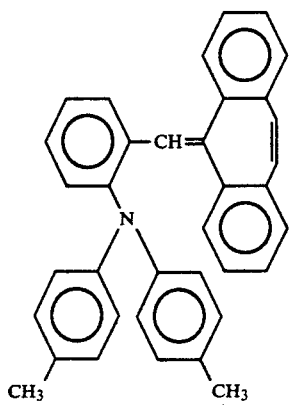

(53)

The novel compounds according to the present invention can be also synthesized in the following manner besides the foregoing synthesis procedure.

Synthesis Example of the above exemplified compound (13):

20 g (66.4 mmol) of p-ditolylaminobenzaldehyde and 23.1 g (69.9 mmol) of 10,11-dihydro-5H-dibenzo[a,d]cycloheptenyl phosphonate were dissolved in 100 cc of DMSO, and admixed with 2.8 g (70.0 mmol) of oily sodium hydride (60%) at room temperature. Then, the mixture was stirred with heating at about 100° C. for 10 hours, and, after cooling, the reaction mixture was poured into water and extracted with ethyl acetate. The organic layer was dried over anhydrous sodium sulfate, and the solvent was removed therefrom under reduced pressure. The residue was recrystallized from a methanol-acetone solvent mixture, whereby 13.7 g of the desired compound (13) was obtained (yield: 46.1%).

Elemental analysis:

| Elemental analysis: | Calculated (%) | Found (%) |
|---|---|---|
| C | 90.53 | 90.50 |
| H | 6.54 | 6.56 |
| N | 2.93 | 2.94 |

$\lambda$max (THF) 357.4 mm

The thus obtained novel 5H-dibenzo[a,d]cycloheptanylidene derivative and 5H-dibenzo[a,d]cycloheptenylidene derivative are very useful as a photoconductive material in the electrophotographic photosensitive member.

According to a preferable embodiment of the present invention, the present compounds represented by the general formula [I] can be used as a charge transport material in an electrophotographic photosensitive member, whose photosensitive layer is functionally divided into a charge generation layer and a charge transport layer. When a compound represented by the general formula [I], where both $R_1$ and $R_2$ in the substituted amino group are aromatic groups, is used as the charge transport material, a particularly good result can be obtained.

It is preferable to form a charge transport layer by coating of a solution of the compound represented by the general formula [I] and a binder in an appropriate solvent, followed by drying. The binder for use in the present invention includes polyacrylate resin, polysulfone resin, polyamide resin, acrylic resin, acrylonitrile resin, methacrylic resin, polyvinyl chloride resin, polyvinyl acetate resin, phenol resin, epoxy resin, polyester resin, alkyd resin, polycarbonate resin, polyurethane or copolymer resin containing at least two of repetition units of these resins, for example, styrene-butadiene copolymer, styrene-acrylonitrile copolymer, styrene-maleic acid copolymer, etc. Furthermore, organic photoconductive polymers such as polyvinylcarbazole, polyvinylanthracene, polyvinylpyrene, etc. can be also used beside said insulating polymers.

A preferable mixing ratio of the present charge transport material to the binder is 10 to 500 parts by weight of the charge transport material to 100 parts by weight of the binder.

The charge transport layer is electrically connected to a charge generation layer as will be described below, and has a function to receive the charge carriers injected from the charge generation layer in the presence of an electric field, and transport the charge carriers up to the surface. The charge transport layer may be provided on the charge generation layer as an overlayer or as an underlayer, but it is preferable to provide the charge transport layer as an overlayer on the charge generation layer. The charge transport layer has a limit to its capacity to transport the charge carriers and its film thickness cannot be made larger as desired. The thickness is usually in a range of 5-30 $\mu$m, preferably 8-20 $\mu$m.

The organic solvent for use in forming such a charge transport layer depends upon the species of a binder to be used, and is preferably selected from those incapable of dissolving the charge generation layer or a primer layer as will be described below. Specifically, the organic solvent for use in the present invention includes, for example, an alcohol such as methanol, ethanol, isopropanol, etc., a ketone such as acetone, methylethylketone, cyclohexanone, etc., an amide such as N,N-dimethyl formamide, N,N-dimethyl acetamide, etc., a sulfoxide such as dimethyl sulfoxide, etc., an ether such as tetrahydrofuran, dioxane, ethyleneglycol monomethyl ether, etc., an ester such as methyl acetate, ethyl acetate, etc., an aliphatic halogenated hydrocarbon such as chloroform, methylene chloride, dichloroethylene, carbon tetrachloride, trichloroethylene, etc., an aromatic hydrocarbon such as benzene, toluene, xylene, ligroin, monochlorobenzene, dichlorobenzene, etc.

The coating is carried out according to any of dip coating, spray coating, spinner coating, bead coating, Meyer bar coating, blade coating, roller coating, curtain coating, etc. The drying is carried out preferably by heating after being tack free at room temperature. Drying by heating can be carried out at a temperature of 30° C. to 200° C. for 5 minutes to 2 hours at rest or with air blowing.

The charge transport layer according to the present invention can contain various additives. The additives include, for example, diphenyl, diphenyl chloride, o-terphenyl, p-terphenyl, dibutyl phthalate, dimethylglycol phthalate, dioctyl phthalate, triphenyl phosphate, methylnaphthalene, benzophenone, chlorinated paraffin, dilauryl thiopropionate, 3,5-dinitrosalicylic acid, various fluorocarbons, etc.

The charge generation layer for use in the present invention can be a discrete vapor deposition layer or coating layer composed of an inorganic charge generating material such as selenium, selenium-tellurium, amorphous silicon, etc., or an organic charge generating material such as a cationic dye, for example, a pyryliumbased dye, a thiopyrilium-based dye, a thiacyanin-based dye, a quinocyanin-based dye, an azulenium-based dye, etc; a squarilium salt-based dye; a phthalocyanine-based pigment; a polycyclic quinone pigment, for example, an anthanthrone-based pigment, a dibenzpyrenequinone-based pigment, a pyranthron-based pigment, etc.; an indigo-based pigment, a quinacridone-based pigment, an azopigment, etc.

Among the charge generating materials for use in the present invention, particularly the azo pigment is diversified, and it is difficult to specify their structures. Structural examples of azo pigments having a particularly excellent effect will be given below.

When the azo pigments are represented by the following general formula:

$$A\text{-}(N=N-Cp)_n,$$

wherein A is a central skeleton, Cp is a coupler portion and n is 2 or 3, typical examples of A can be given below:

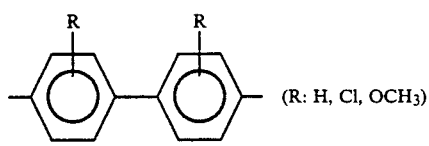
(R: H, Cl, OCH₃)    A-1

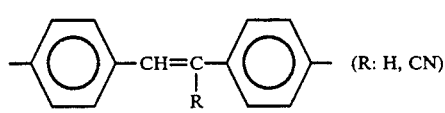
(R: H, CN)    A-2

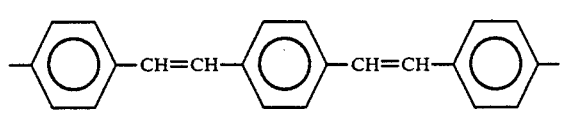
A-3

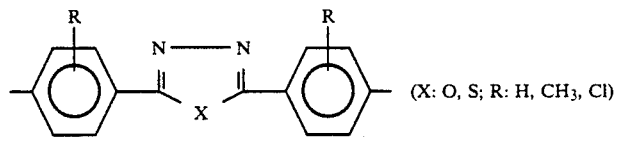
(X: O, S; R: H, CH₃, Cl)    A-4

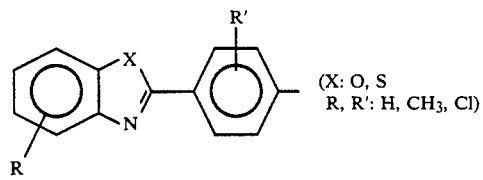
(X: O, S
R, R': H, CH₃, Cl)    A-5

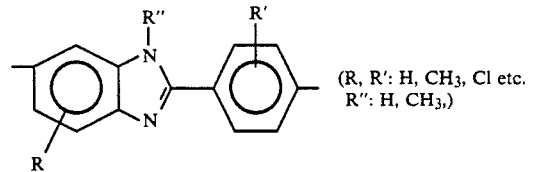
(R, R': H, CH₃, Cl etc.
R'': H, CH₃,)    A-6

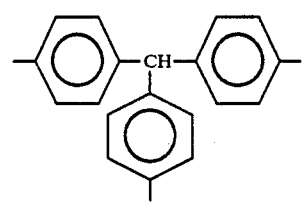
A-7

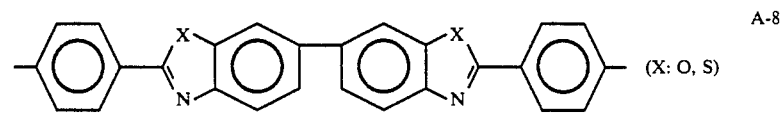
(X: O, S)    A-8

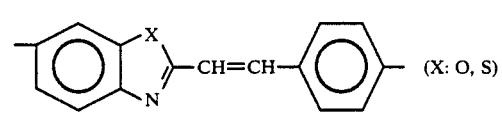
(X: O, S)    A-9

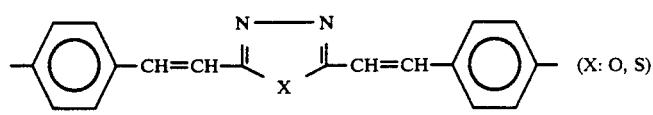 A-10
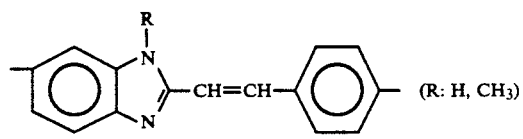 A-11
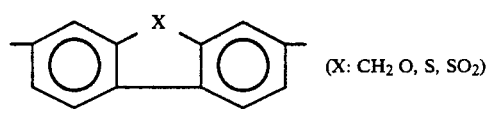 A-12
A-13
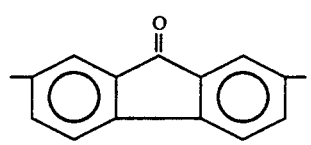
A-14
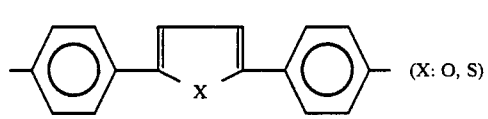
A-15
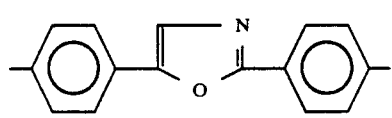
A-16
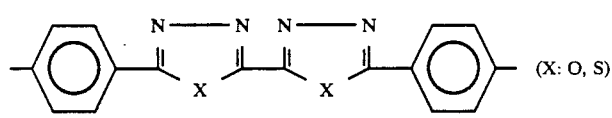
A-17
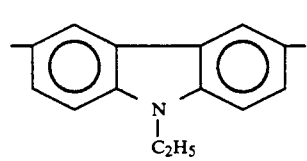
A-18
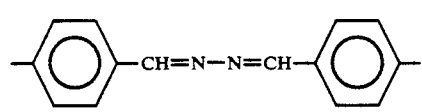
A-19
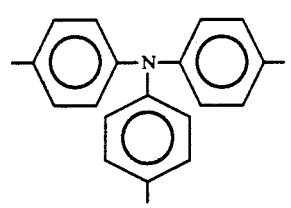
A-20
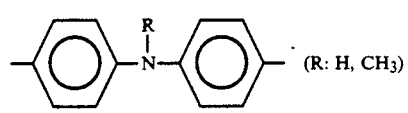
Typical examples of Cp can be given below:

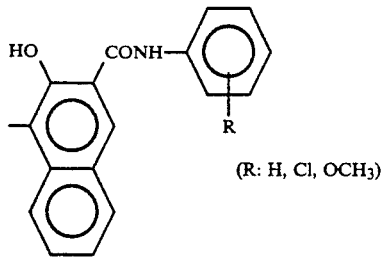
Cp-1
(R: H, Cl, OCH₃)
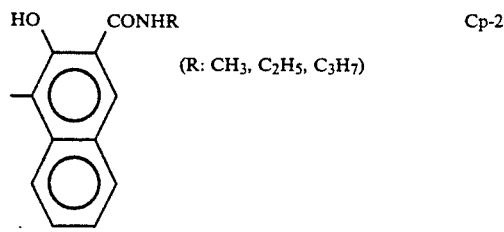
Cp-2
(R: CH₃, C₂H₅, C₃H₇)
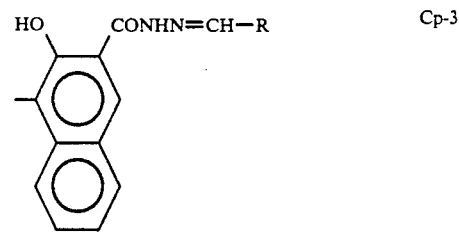
Cp-3
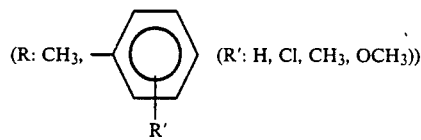
(R: CH₃,    )    (R': H, Cl, CH₃, OCH₃))
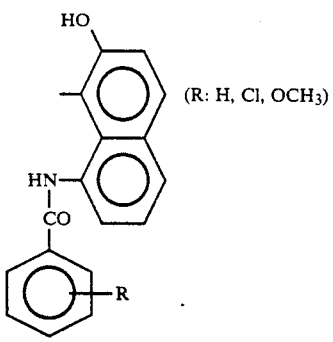
Cp-4
(R: H, Cl, OCH₃)
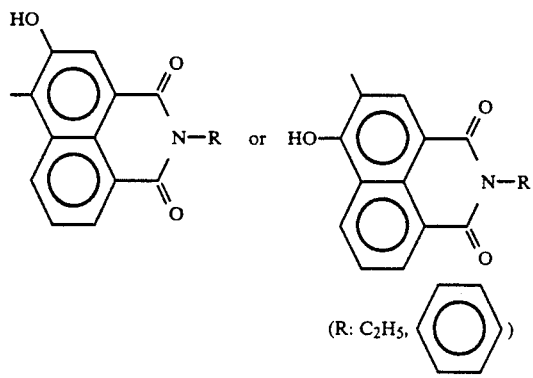
Cp-5
(R: C₂H₅,    )

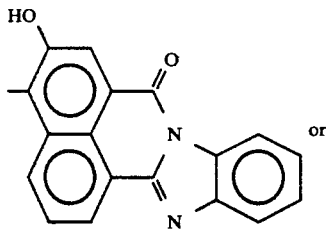

or

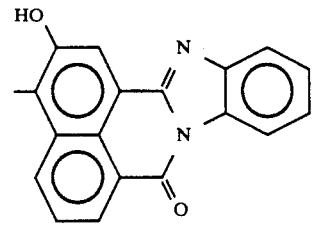

Cp-6

Cp-7

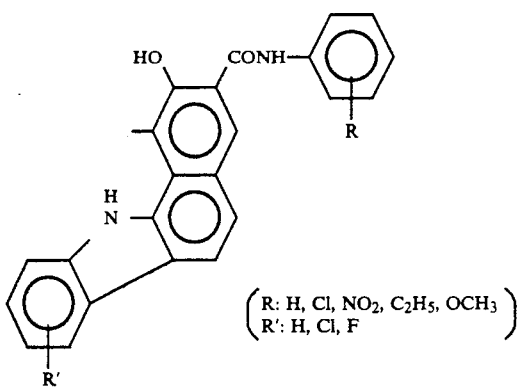

(R: H, Cl, NO₂, C₂H₅, OCH₃
R': H, Cl, F)

Through an appropriate combination of the central skeleton A and the coupler Cp, a pigment serving as a charge generating material can be formed.

The charge generation layer can be formed by dispersing said charge generating material in an appropriate binder and coating a support with the resulting dispersion, or by vapor depositing a film on a support from the said charge generating material by means of a vacuum vapor deposition apparatus.

The binder for use in forming a charge generation layer by coating can be selected from a broad range of insulating resins and also from organic photoconductive polymers such as poly-N-vinylcarbazole, polyvinylanthracene, polyvinylpyrene, etc. Preferably, it is selected from such insulating resins as polyvinylbutyral, polyarylate (polycondensate of bisphenol A and phthalic acid, etc.), polycarbonate, polyester, phenoxy resin, polyvinyl acetate, acrylic resin, polyacrylamide resin, polyamide, polyvinyl pyridine, cellulose-based resin, urethane resin, epoxy resin, casein, polyvinyl alcohol, polyvinylpyrrolidone, etc. An appropriate resin content in the charge generation layer is not more than 80% by weight, preferably not more than 40% by weight.

The organic solvent for use in the coating includes an alcohol such as methanol, ethanol, isopropanol, etc., a ketone such as acetone, methylethylketone, cyclohexane, etc., an amide such as N,N-dimethyl formamide, N,N-dimethyl acetamide, etc., a sulfoxide such as dimethyl sulfoxide, etc., an ether such as tetrahydrofuran, dioxane, ethyleneglycol monomethyl ether, etc., an ester such as methyl acetate, ethyl acetate, etc., an aliphatic halogenated hydrocarbon such as chloroform, methylene chloride, dichloroethylene, carbon tetrachloride, trichloroethylene, etc., an aromatic hydrocarbon such as benzene, toluene, xylene, ligroin, monochlorobenzene, dichlorobenzene, etc.

The coating can be carried out according to any of dip coating, spray coating, spinner coating, bead coating, Meyer bar coating, blade coating, roller coating, curtain coating, etc. Preferably the charge generation layer contains said organic photoconductive material as much as possible to obtain a sufficient absorbance and is a thin film layer having a film thickness of e.g. not more than 5 μm, preferably 0.01-1 μm, to shorten the flying distance of generated charge carriers. This is due to the fact that most of the incident light quantity must be absorbed in the charge generation layer to form a larger amount of charge carriers and the generated charge carriers must be injected into the charge transport layer without any deactivation by recombination or trapping of the generated charge carriers.

A photosensitive layer of laminated structure type composed of the charge generation layer and the charge transport layer is provided on an electroconductive support. The electroconductive support for use in the present invention includes an electroconductive support by itself, for example, composed of aluminum, aluminum alloy, copper, zinc, stainless steel, vanadium, molybdenum, chromium, titanium, nickel, indium, gold, platinum, or the like; plastics having a film layer made from aluminum, aluminum alloy, indium oxide, tin oxide, indium oxide-tin oxide alloy, or the like by vacuum vapor deposition, where the plastics include polyethylene, polypropylene, polyvinyl chloride, polyethylene terephthalate, acrylic resin, polyfluoroethylene, etc.;

plastics or electroconductive support coated with electroconductive particles of, for example, aluminum powder, titanium oxide, tin oxide, zinc oxide, carbon black, silver particles, or the like, together with an appropriate binder; plastics or paper impregnated with electroconductive particles; and plastics containing an electroconductive polymer, etc.

Between the electroconductive support and the photosensitive layer, a primer layer having both barrier function and adhesive function can be provided. The primer layer can be made from casein, polyvinyl alcohol, nitrocellulose, ethylene-acrylate copolymer, polyamide (nylon 6, nylon 66, nylon 610, copolymerized nylon, alkoxymethylated nylon, etc.), polyurethane, gelatin, aluminum oxide, or the like.

The appropriate thickness of the primer layer is 0.1-5 μm, preferably 0.5-3 μm.

In the case of a photosensitive member comprising an electroconductive support, a charge generation layer and a charge transport layer, laid one upon another in this order, the charge transport material is positive hole-transportable, and thus the surface of the charge transport layer must be negatively charged. After charging, the positive holes formed at light exposed parts in the charge generation layer by light exposure are injected into the charge transport layer and reach the surface of the charge transport layer to neutralize the negative charges. Thus, attenuation of surface potentials is made thereby, and an electrostatic contrast is formed between the light exposed parts and the unexposed parts. At the development, a positively chargeable toner must be used.

The present electrophotographic photosensitive member can be utilized not only in electrophotographic copying machines, but also can be widely utilized in electrophotographic application fields such as laser printers CRT printers, electrophotographic reproduction system, etc.

The present electrophotographic photosensitive member has a high sensitivity and also has such an advantage as a small fluctuation in the light portion potential and the dark portion potential when subjected to repeated charging and light exposure.

The present 5H-dibenzo[a,d]cycloheptanylidene derivative and 5H-dibenzo[a,d]cycloheptanylidene derivative are useful, not only for the electrophotographic photosensitive member, but also as an organic electroconductive material for the electrophotographic reproduction system, photosensors, etc. and also can be used as a fluorescent whitening agent.

The present invention will be described in detail below, referring to Examples.

EXAMPLE 1

Synthesis of Exemplified Compound (39)

154 ml (1.34 moles) of benzyl chloride (d=1.10) and 206 ml (1.2 moles) of triethyl phosphite (d=0.969) were slowly heated on an oil bath with stirring, and refluxed for 20 hours with stirring while keeping the oil bath at about 160° C. to about 180° C. After the reaction, the reaction mixture was subjected to distillation under reduced pressure whereby 215.4 g of diethylbenzyl phosphonate was obtained (yield: 78.6%). The boiling point was 134.5°-136.0° C. (7 mmHg). The infrared absorption spectrum (neat method) is shown in FIG. 1.

Then, 55.0 ml (1.25 moles) of fuming nitric acid (d=1.52, 94%) was placed in a three-necked flask having a capacity of 200 ml, and after the flask inside temperature was cooled to −10° to −5° C. with stirring, 61.6 g (0.27 moles) of the thus obtained diethylbenzyl phosphonate was slowly added thereto dropwise over one hour. After the dropwise addition, the mixture was stirred at the same temperature as above for 30 minutes, and then the reaction mixture was poured into about 600 ml of ice water, and extracted with about 300 ml of ethyl acetate. The organic layer was washed with an aqueous saturated NaCl solution and dried over anhydrous sodium sulfate. The solvent was removed therefrom by distrillation under reduced pressure. Then, the residue was further distilled under reduced pressure, whereby 61.3 g of diethyl-4-nitrobenzyl phosphonate was obtained (yield: 83.1%). The boiling point was 199°-201.0° C. (3 mmHg). Elemental analysis as $C_{11}H_{16}NO_5P$ was as follows:

|  | C % | H % | N % |
| --- | --- | --- | --- |
| Calculated | 48.36 | 5.90 | 5.13 |
| Found | 48.39 | 5.92 | 5.10 |

Figure 2:
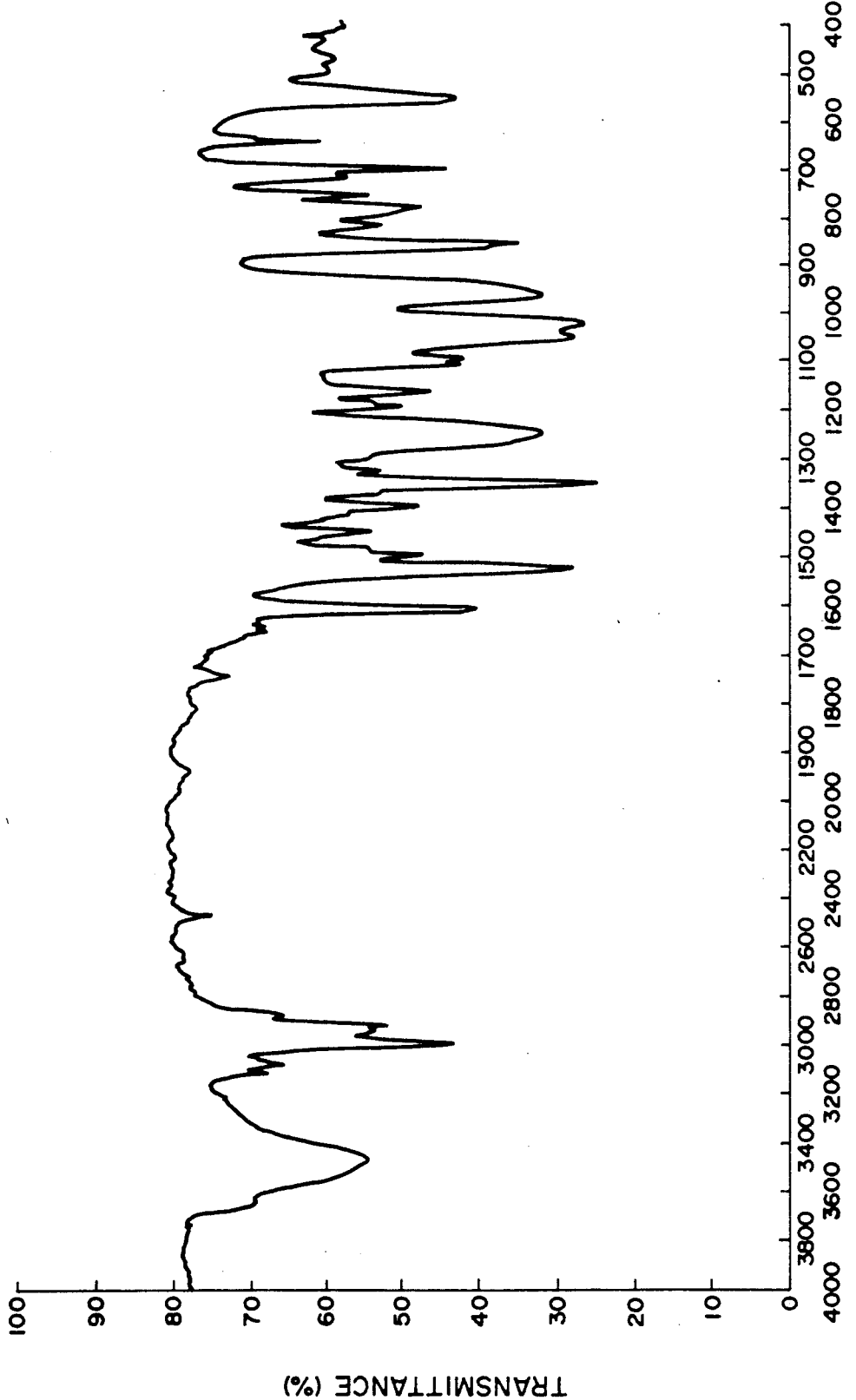

The infrared absorption spectrum (neat method) is shown in FIG. 2.

150 ml of dimethyl sulfoxide was admixed with 3.60 g (about 90 mmoles) of oily sodium hydride (about 60%) at room temperature. After the addition, the mixture was heated over an oil bath to an inside temperature of about 70° C., and stirred as such for about one hour. Then, the reaction mixture was cooled to room temperature, and a solution of 25.1 g (92 m moles) of the previously obtained diethyl-4-nitrobenzyl phosphonate and 10.0 g (48.5 m moles) of 5H-dibenzo[a,d]cycloheptene-5-on in 50 ml of dimethyl sulfoxide was added thereto dropwise. After the dropwise addition, the mixture was stirred at room temperature for 15 minutes, and then further stirred with heating at an inside temperature of 70° to 80° C. for 2 hours over an oil bath. After the end of reaction, the mixture was cooled to room temperature, poured into about 1 l of an aqueous saturated NaCl solution, and extracted with ethyl acetate. The organic layer was dried over anhydrous sodium sulfate and then the solvent was removed therefrom under reduced pressure. The residue was admixed with methanol, and the thus precipitated crystal was recovered therefrom by filtration. The thus obtained crystal was recrystallized from methanol-acetone solvent mixture, whereby 10.94 g of 5-(4-nitrobenzylidene)-5H-dibenzo[a,d]cycloheptene was obtained (yield: 69.3%). The melting point was 151.5°-152.5° C. The elemental analysis as $C_{22}H_{15}NO_2$ was as follows:

|  | C % | H % | N % |
| --- | --- | --- | --- |
| Calculated | 81.21 | 4.65 | 4.30 |
| Found | 81.18 | 4.69 | 4.31 |

Figure 3:
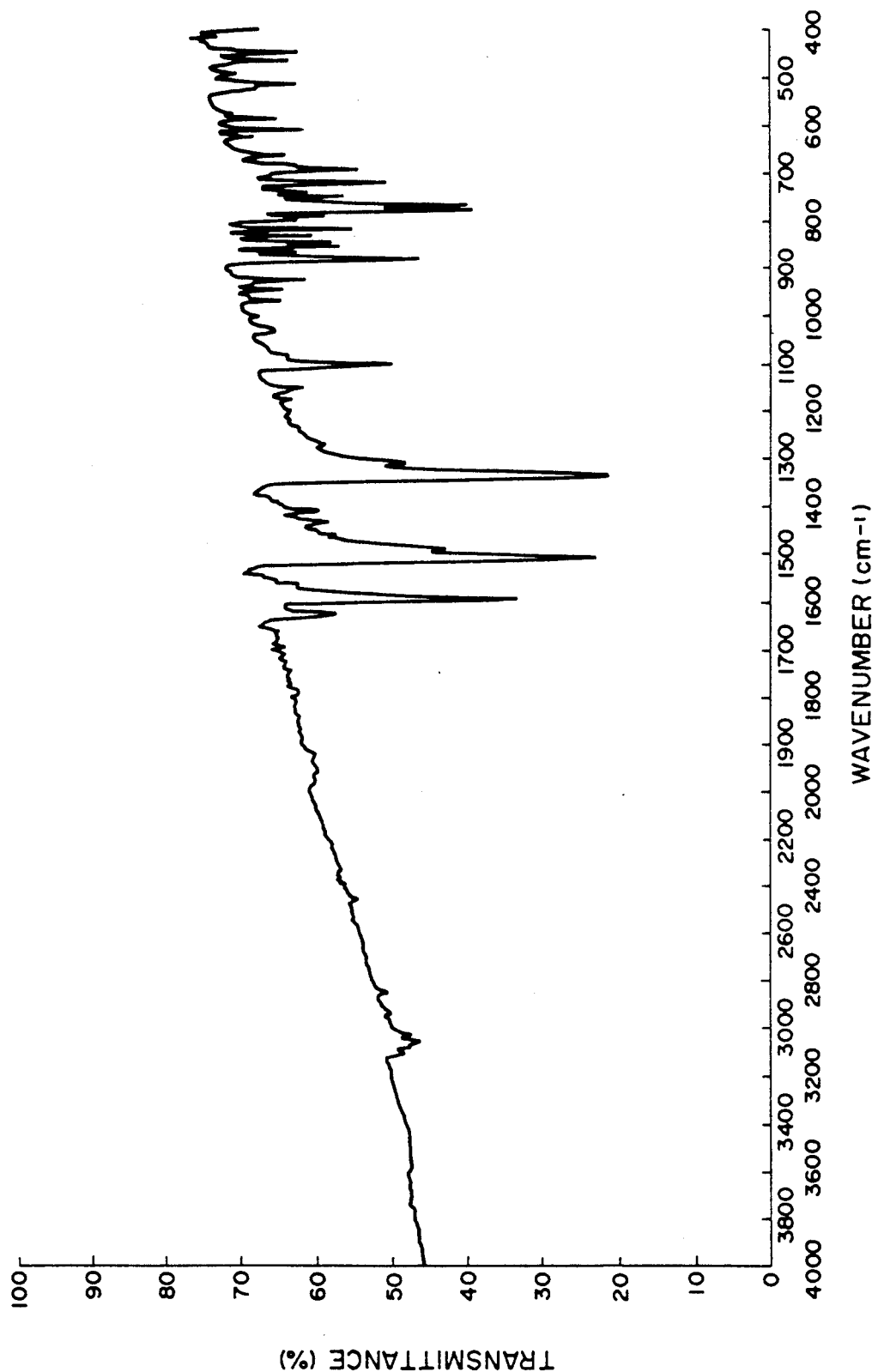
FIGS. 3 to 13 are infrared absorption spectral diagrams according to a KBr tablet method.

The infrared absorption spectrum (KBr tablet method) is given in FIG. 3.

10.0 g (30.7 m moles) of 5-(4-nitrobenzylidene)-5H-dibenzo[a,d]cycloheptene, 8.0 g (143 m moles) of reductive iron powder, and 2.70 ml (30.6 m moles) of concentrated hydrochloric acid (d: 1.18, 35%) were added to 150 ml of N,N-dimethyl formamide, and the mixture was heated at an inside temperature of about 70° C., and stirred at that temperature with heating for 3 hours. After the end of reaction, the mixture was cooled over an ice-water bath, admixed with about 12.4 ml of an aqueous 10% NaOH solution, stirred and subjected to filtration by suction. The filtrate was poured into about 1 l of an aqueous saturated NaCl solution, and extracted with ethyl acetate. The organic layer was dried over anhydrous sodium sulfate, and then the solvent was removed therefrom under reduced pressure. The residue was admixed with methanol, and the precipitated crystal was recovered therefrom by filtration. The thus obtained crystal was recrystallized from methanol, whereby 8.41 g of 5-(4-aminobenzylidene)-5H-dibenzo[a,d]cycloheptene was obtained (yield: 92.7%). The melting point was 119°–120.0° C. Elemental analysis as $C_{22}H_{17}N$ was as follows:

|  | C % | H % | N % |
| --- | --- | --- | --- |
| Calculated | 89.46 | 5.80 | 4.74 |
| Found | 89.41 | 5.83 | 4.76 |

Figure 4:
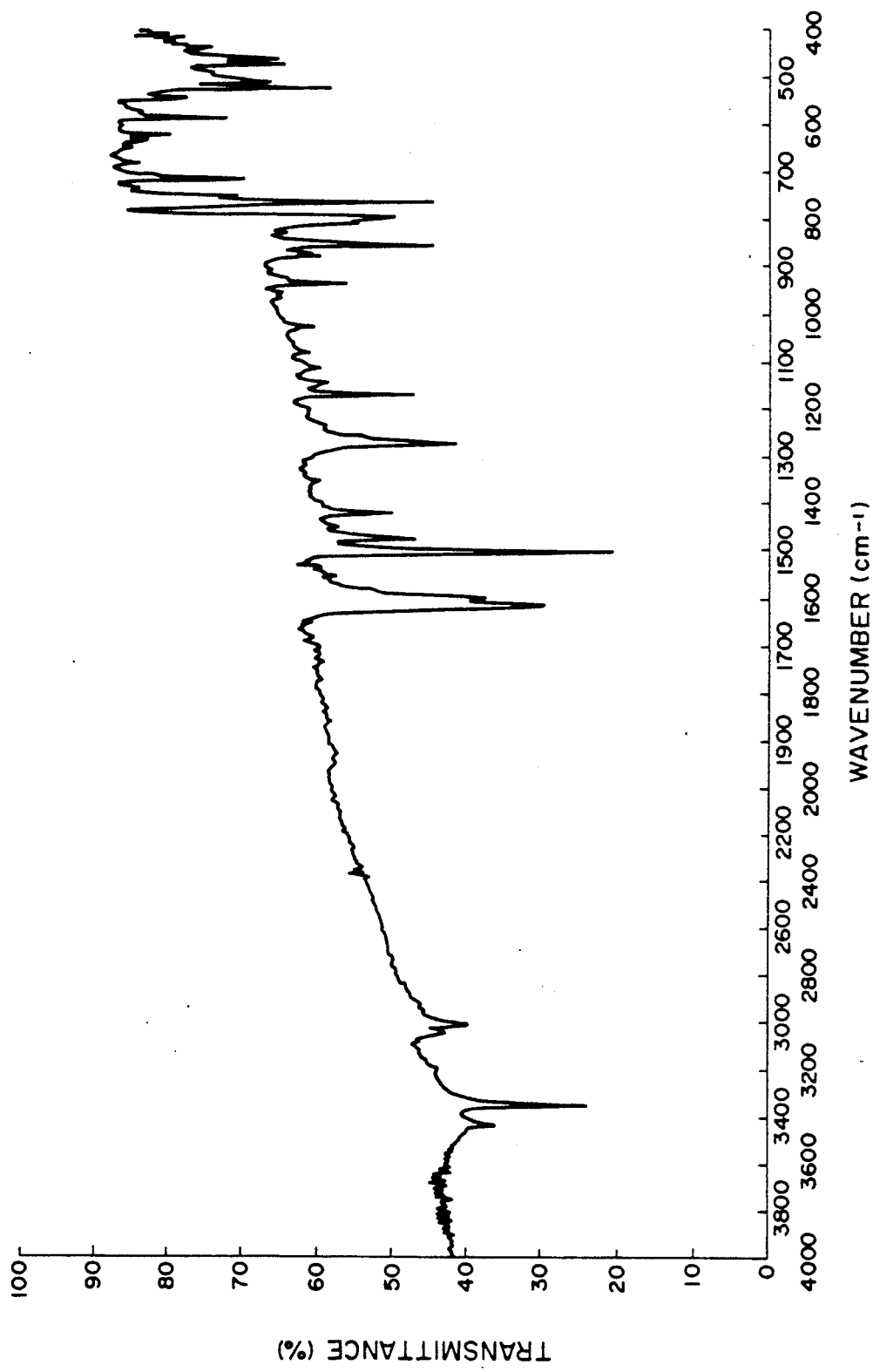

The infrared absorption spectrum (KBr tablet method) is shown in FIG. 4.

7.90 g (26.7 m moles) of the previously obtained 5-(4-amino-benzylidene)-5H-dibenzo[a,d]cycloheptene, 22.0 g (101 m mole) of p-iodotoluene, 11.0 g (79.6 m moles) of anhydrous potassium carbonate and 2.2 g of copper powder were added to 30 ml of o-dichlorobenzene, and the resulting mixture was stirred and refluxed over an oil bath kept at about 190° C. for 7 hours. After the end of reaction, the reaction mixture was subjected to filtration by suction, and the filtrate was washed successively with an aqueous 3–5% sodium thiosulfate solution and an aqueous saturated NaCl solution. The organic layer was dried over anhydrous sodium sulfate and then the solvent was removed therefrom under reduced pressure. The residue was admixed with about 60 ml of acetone, and the precipitated crystal was recovered therefrom by filtration, and recrystallized from ethyl acetate-n-hexane solvent mixture, whereby 9.52 g of 5-[4(di-p-tolylamino)benzylidene]-5H-dibenzo[a,d]cycloheptene was obtained (yield: 75.0%). The melting point was 168.0°–169.0° C. Elemental analysis as $C_{36}H_{29}N$ was as follows:

|  | C % | H % | N % |
| --- | --- | --- | --- |
| Calculated | 90.90 | 6.15 | 2.95 |
| Found | 90.85 | 6.17 | 2.98 |

Figure 5:
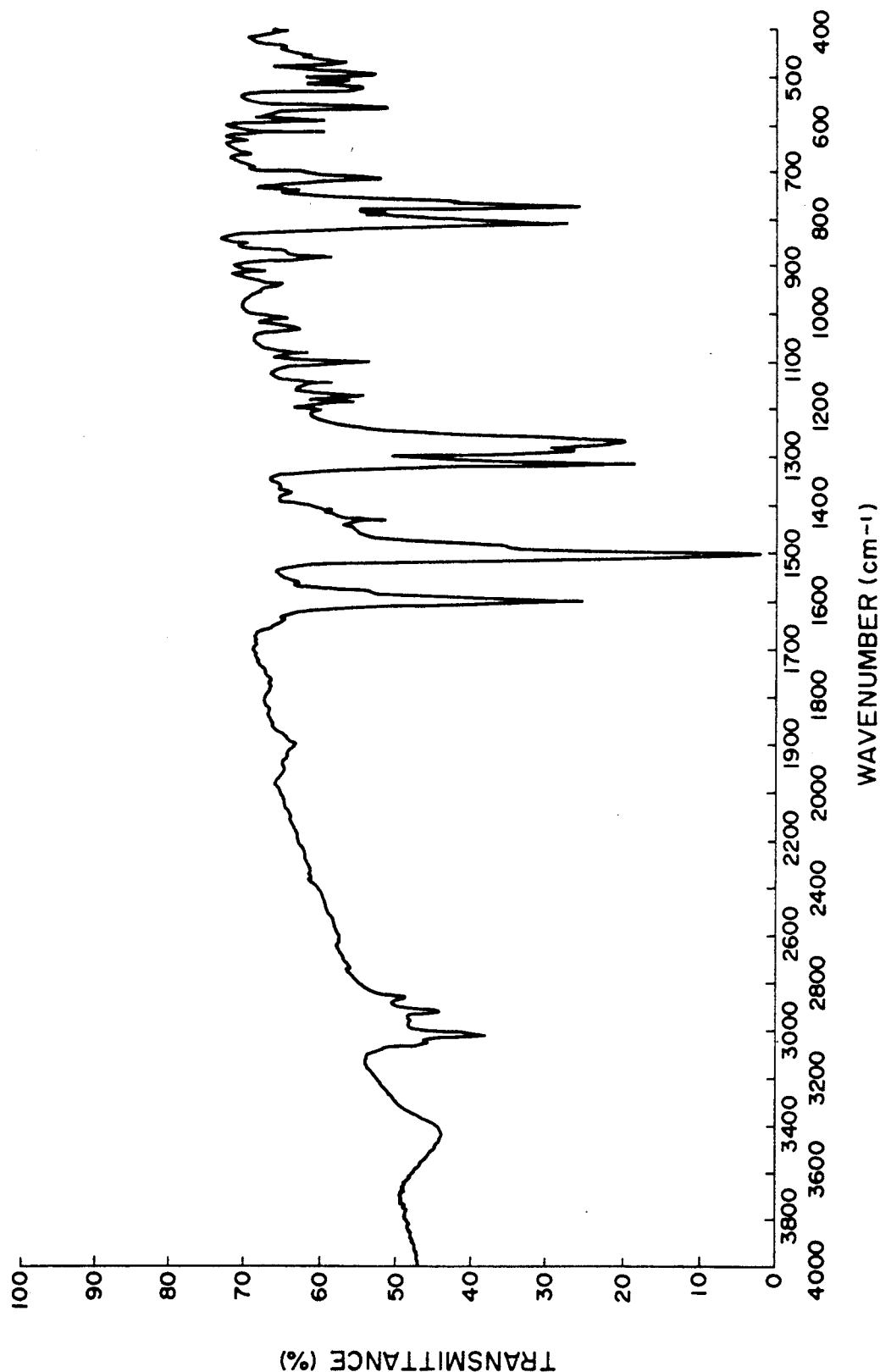

The infrared absorption spectrum (KBr tablet method) is shown in FIG. 5.

EXAMPLE 2

Synthesis of Exemplified Compound (36)

10.0 g (33.9 m moles) of 5-(4-aminobenzylidene)-5H-dibenzo[a,d]cycloheptene obtained in the same manner as in Example 1, 42.0 g (206 m moles) of iodobenzene, 14.1 g (102 m moles) of anhydrous potassium carbonate and 2.80 g of copper powder were stirred and refluxed over an oil bath kept at about 200° C. for 4 hours. After the end of reaction, the reaction mixture was subjected to filtration by suction, and the filtrate was washed successively with an aqueous 3–5% sodium thiosulfate solution and an aqueous saturated NaCl solution. The organic layer was dried over anhydrous sodium sulfate and the solvent was removed therefrom under reduced pressure. The residue was admixed with about 80 ml of methanol, and the precipitated crystal was recovered therefrom by filtration, and recrystallized from methanol-acetone solvent mixture, whereby 11.2 g of 5-(4-diphenylaminobenzylidene)-5H-dibenzo[a,d]cycloheptene was obtained (yield: 73.8%). The melting point was 83.5°–84.5° C. Elemental analysis as $C_{34}H_{25}N$ was as follows:

|  | C % | H % | N % |
| --- | --- | --- | --- |
| Calculated | 91.24 | 5.63 | 3.13 |
| Found | 91.27 | 5.64 | 3.29 |

Figure 6:
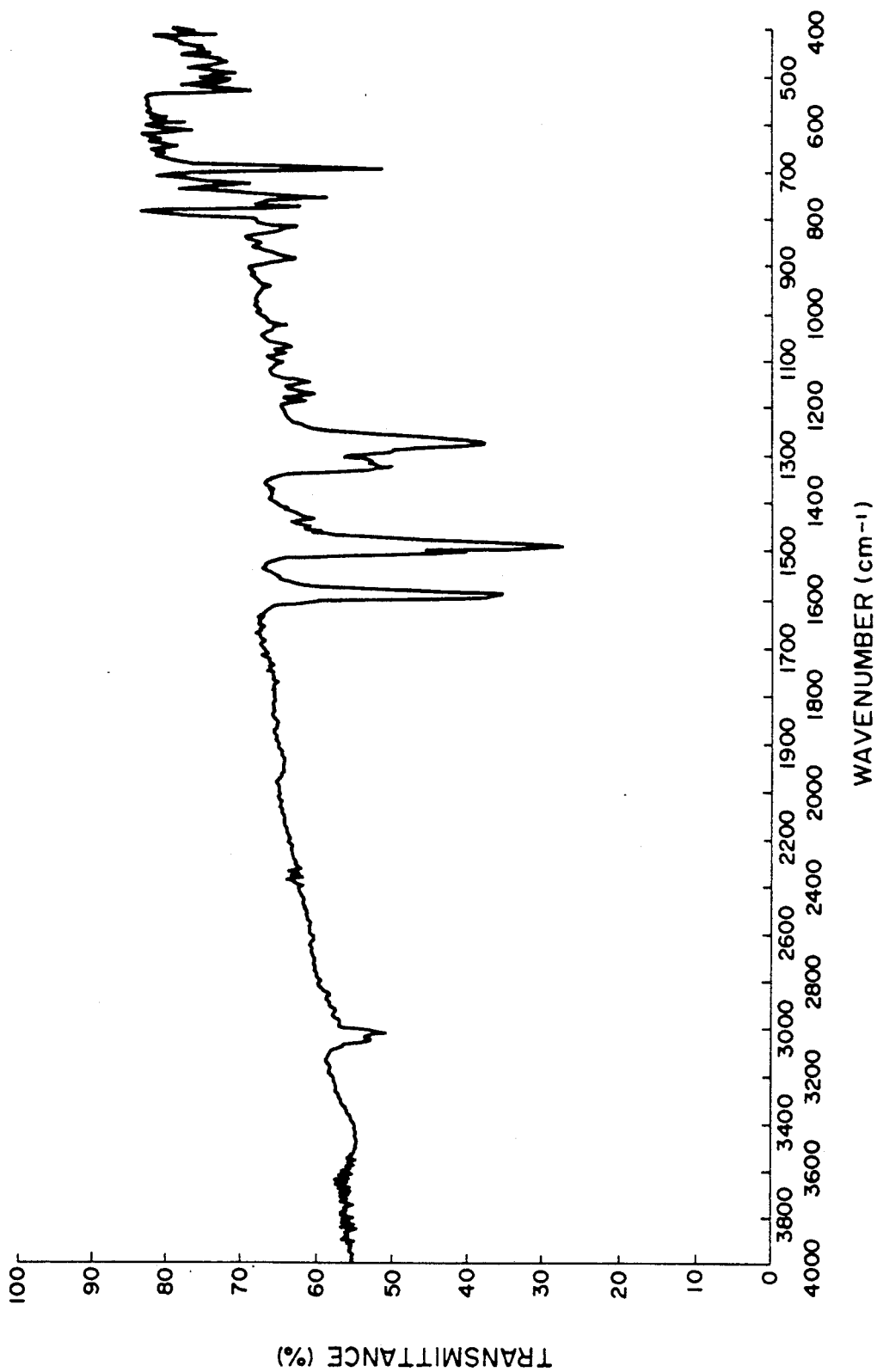

The infrared absorption spectrum (KBr tablet method) is shown in FIG. 6.

EXAMPLE 3

Synthesis of Exemplified Compound (27)

8.0 g (27.1 m mole) of 5-(4-aminobenzylidene)-5H-dibenzo[a,d]cycloheptene obtained in the same manner as in Example 1 was added to 30 ml of N,N-dimethyl formamide, and then 3.25 g (about 81.3 m moles) of oily sodium hydride (about 60%) was slowly added thereto at room temperature. After the addition, the mixture as such was stirred at room temperature for 15 minutes, and then 12.6 g (80.8 m moles) of ethyl iodide was added thereto. The mixture was stirred at room temperature for 30 minutes, and subjected to reaction at 80° C. for 2 hours. After being left for cooling down to room temperature, the reaction mixture was poured into about 200 ml of an aqueous saturated sodium chloride solution, and extracted with ethyl acetate. The organic layer was dried over anhydrous sodium sulfate, and the solvent was removed therefrom under reduced pressure. The residue was admixed with about 60 ml of methanol, and the precipitated crystal was recovered therefrom by filtration and recrystallized from methanol-acetone solvent mixture, whereby 7.91 g of 5-(4-diethylaminobenzylidene)-5H-dibenzo[a,d]cycloheptene was obtained (yield: 83.0%). The melting point was 109.0°–110.0° C., and elemental analysis as $C_{26}H_{25}N$ was as follows:

|  | C % | H % | N % |
| --- | --- | --- | --- |
| Calculated | 88.85 | 7.17 | 3.98 |
| Found | 88.81 | 7.19 | 3.40 |

Figure 7:
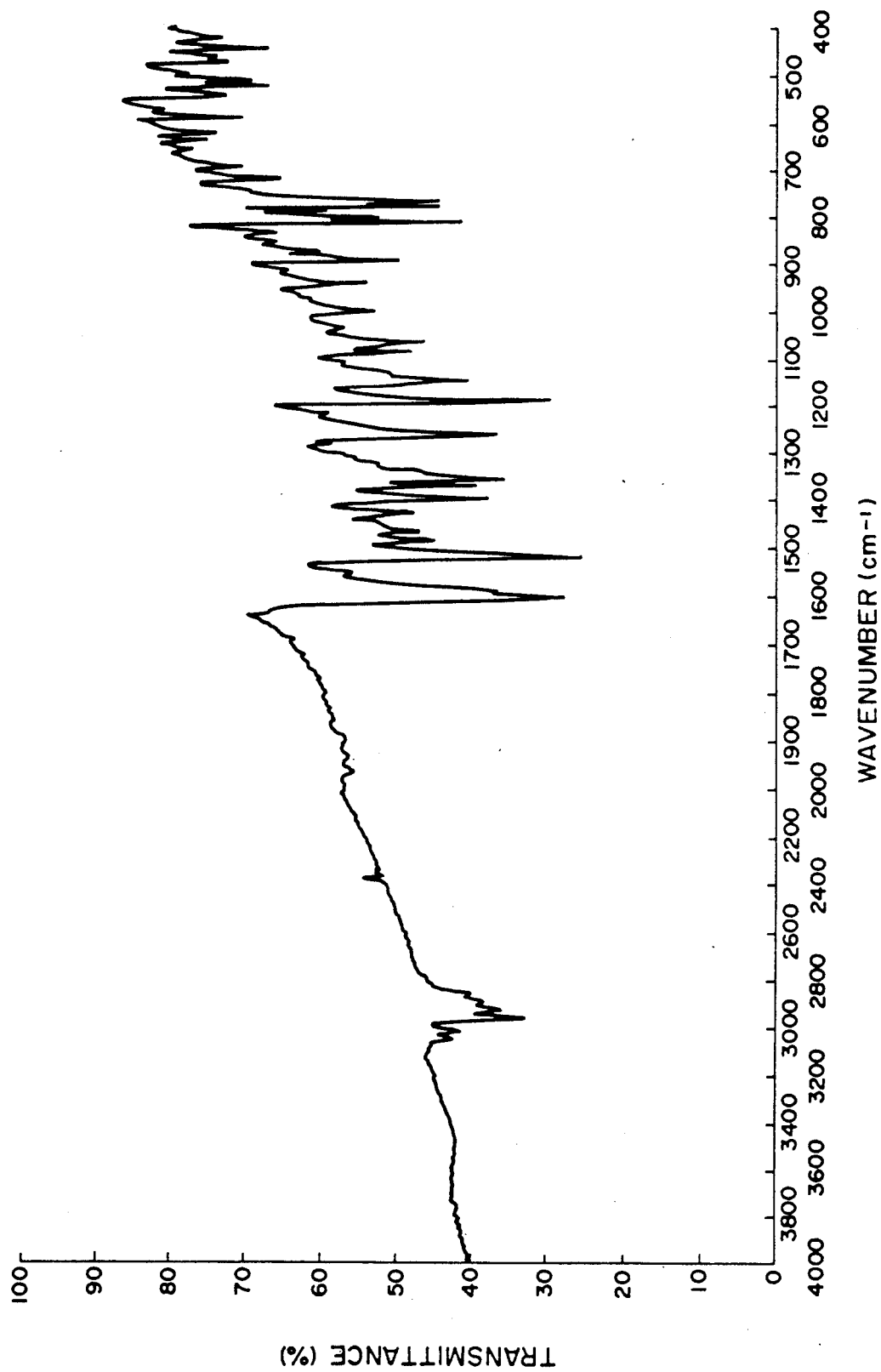

The infrared absorption spectrum (KBr tablet method) is shown in FIG. 7.

EXAMPLE 4

Synthesis of Exemplified Compound (13)

5.0 g (16.8 m moles) of 5-(4-aminobenzylidene)-5H-dibenzo[a,d]cycloheptene synthesized in the same manner as in Example 1, using 5H-dibenzo[a,d]cycloheptene-5-on in place of 5H-dibenzo[a,d]cycloheptene-5-on of Example 1, 14.0 g (64.2 m moles) of p-iodotoluene, 7.0 g (50.6 m moles) of anhydrous potassium carbonate and 1.4 g of copper powder were added to 15 ml of nitrobenzene, and the mixture was stirred and refluxed for 5 hours. After the end of reaction, the reaction mixture was subjected to filtration by suction, and the filtrate was washed successively with an aqueous 3–5% sodium thiosulfate solution and an aqueous saturated NaCl solution. The organic layer was dried over anhydrous sodium sulfate, and the solvent was removed therefrom under reduced pressure. The residue was admixed with about 50 ml of n-hexane, and the precipitated crystal was recovered therefrom by filtration, and recrystallized from ethyl acetate-n-hexane solvent mixture, whereby 5.9 g of 5-[4-(di-p-tolylamino)benzylidene]-5H-dibenzo[a,d]cycloheptene was obtained (yield: 73.5%). The melting point was 158.5°–159.7° C., and elemental analysis as $C_{36}H_{31}N$ was as follows:

|  | C % | H % | N % |
|---|---|---|---|
| Calculated | 90.53 | 6.54 | 2.93 |
| Found | 90.50 | 6.56 | 2.94 |

Figure 8:
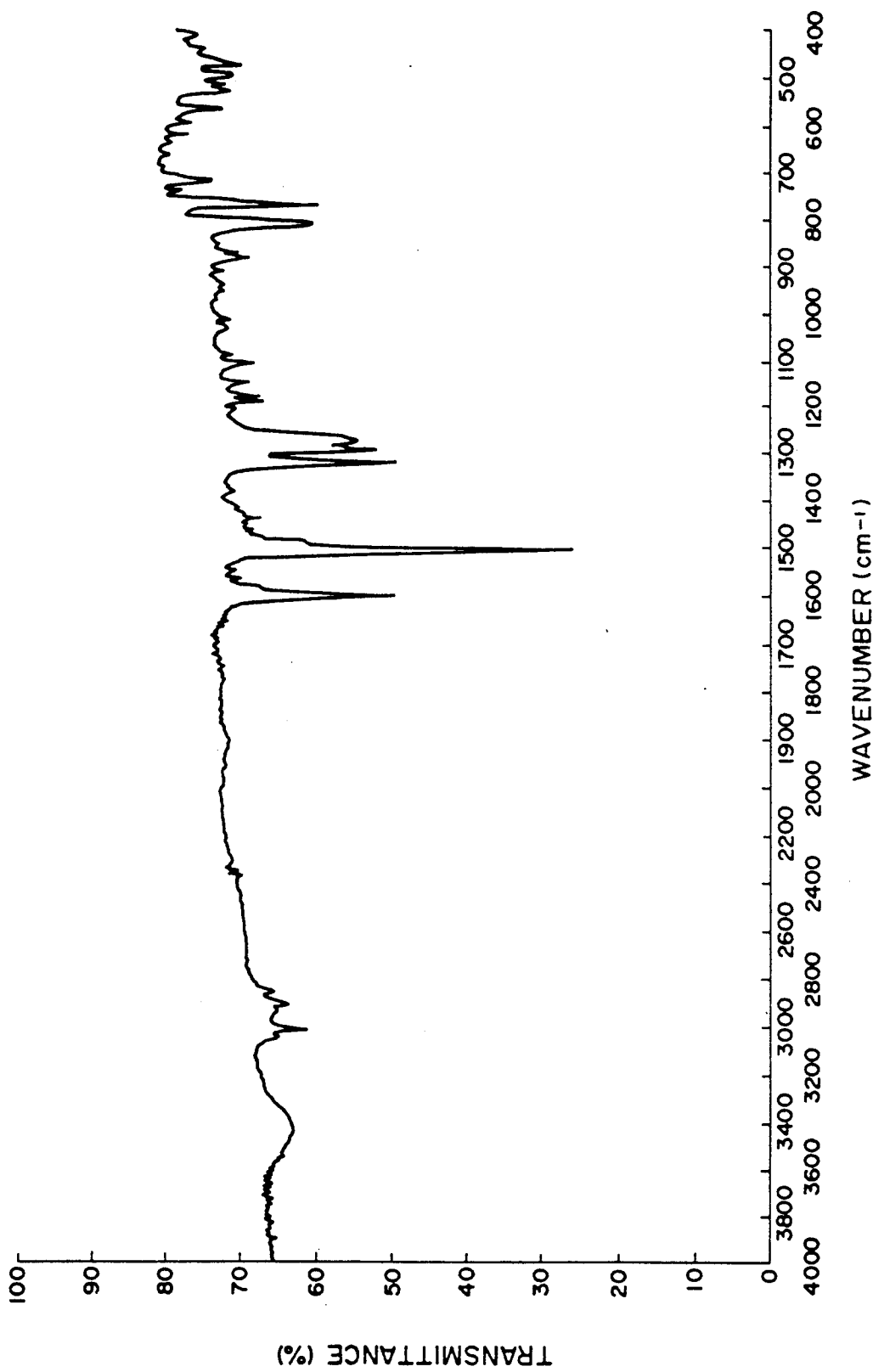

The infrared absorption spectrum (KBr tablet method) is shown in FIG. 8.

EXAMPLE 5

Synthesis of Exemplified Compound (1)

5.0 g (16.8 m moles) of 5-(4-aminobenzylidene)-5H-dibenzo[a,d]cycloheptene obtained in the same manner as in Example 4 was added to 20 ml of tetrahydrofuran, and 2.1 g (about 52.5 m mole) of oily sodium hydride (about 60%) was slowly added thereto at room temperature. After the addition, the mixture as such was stirred at room temperature for 10 minutes, and admixed with 9.54 g (67.2 m moles) of methyl iodide. The mixture was stirred at room temperature for 15 minutes, and then refluxed with heating for 3 hours.

After being left for cooling down to room temperature, the reaction mixture was poured into about 100 ml of water, and the precipitated crystal was recovered therefrom by filtration, and recrystallized from isopropyl ether-ethyl acetate solvent mixture, whereby 4.37 g of 5-(4-dimethylaminobenzylidene)-5H-dibenzo[a,d]cycloheptene was obtained (yield: 79.9%). Elemental analysis as $C_{24}H_{23}N$ was as follows:

|  | C % | H % | N % |
|---|---|---|---|
| Calculated | 88.58 | 7.12 | 4.30 |
| Found | 88.54 | 7.12 | 4.34 |

EXAMPLE 6

Synthesis of Exemplified Compound (52)

Figure 9:
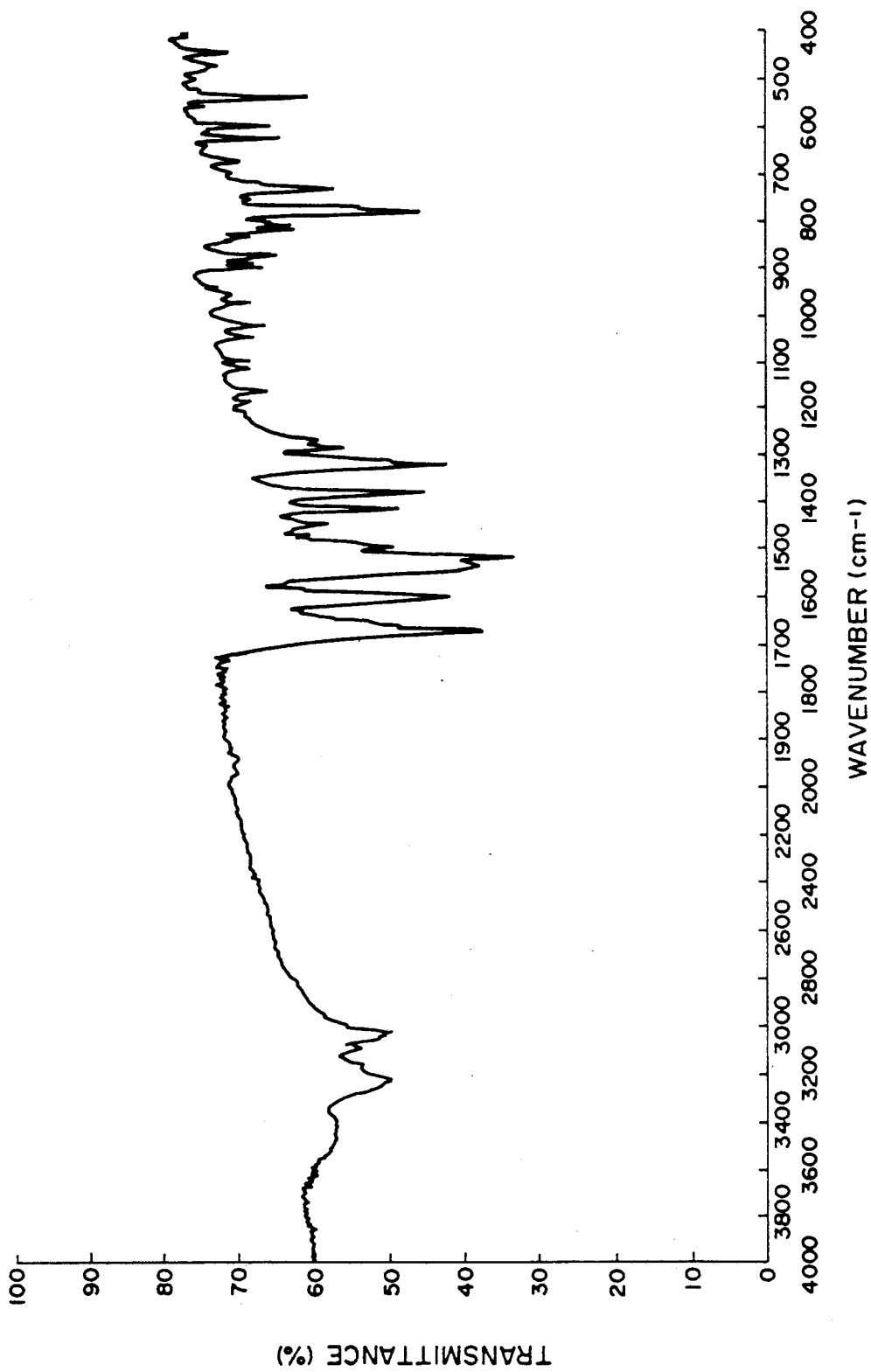

10.0 g (33.9 m moles) of 5-(4-aminobenzylidene)-5H-dibenzo[a,d]cycloheptene obtained in the same manner as in Example 1 and 4.15 g (40.6 m moles) of acetic anhydride were added to 50 ml of toluene, and the mixture was refluxed with heating for 3 hours. After being left for cooling, the reaction mixture was poured into 200 ml of water, and the precipitated crystal was recovered therefrom by filtration and washed with water and then with methanol, whereby 10.6 g of 5-(4-acetylaminobenzylidene)-5H-dibenzo[a,d]cycloheptene was obtained (yield: 92.7%). The melting point was 125.0°–126.0° C. The infrared absorption spectrum (KBr tablet method) is shown in FIG. 9.

8.0 g (23.7 m moles) of the thus obtained 5-(4-acetylaminobenzylidene)-5H-dibenzo[a,d]cycloheptene, 7.75 g (35.5 m moles) of p-iodotoluene, 3.70 g (26.8 m moles) of anhydrous potassium carbonate and 1.80 g of copper powder were added to 15 ml of p-cymene and stirred and refluxed for 5 hours. After the end of reaction, the reaction mixture was subjected to filtration by suction, and the filtrate was successively washed with an aqueous 3–5% sodium thiosulfate solution and an aqueous saturated NaCl solution. The organic layer was dried over anhydrous sodium sulfate, and the solvent was removed therefrom under reduced pressure. The residue was dissolved in 40 ml of tetrahydrofuran and admixed with 2.70 (50.0 m moles) of sodium methylate at room temperature. The mixture as such was stirred at room temperature for one hour, and then the reaction mixture was poured into 150 ml of water. The precipitated crystal was recovered therefrom by filtration, and recrystallized from ethanol-methylethylketone solvent mixture, whereby 5.81 g of 5-[4-(p-tolylamino)benzylidene]-5H-dibenzo[a,d]cycloheptene was obtained (yield: 63.6%). The melting point was 174.0°–175.0° C., and elemental analysis as $C_{29}H_{23}N$ was as follows:

|  | C % | H % | N % |
|---|---|---|---|
| Calculated | 90.35 | 6.01 | 3.63 |
| Found | 90.34 | 6.00 | 3.66 |

Figure 10:
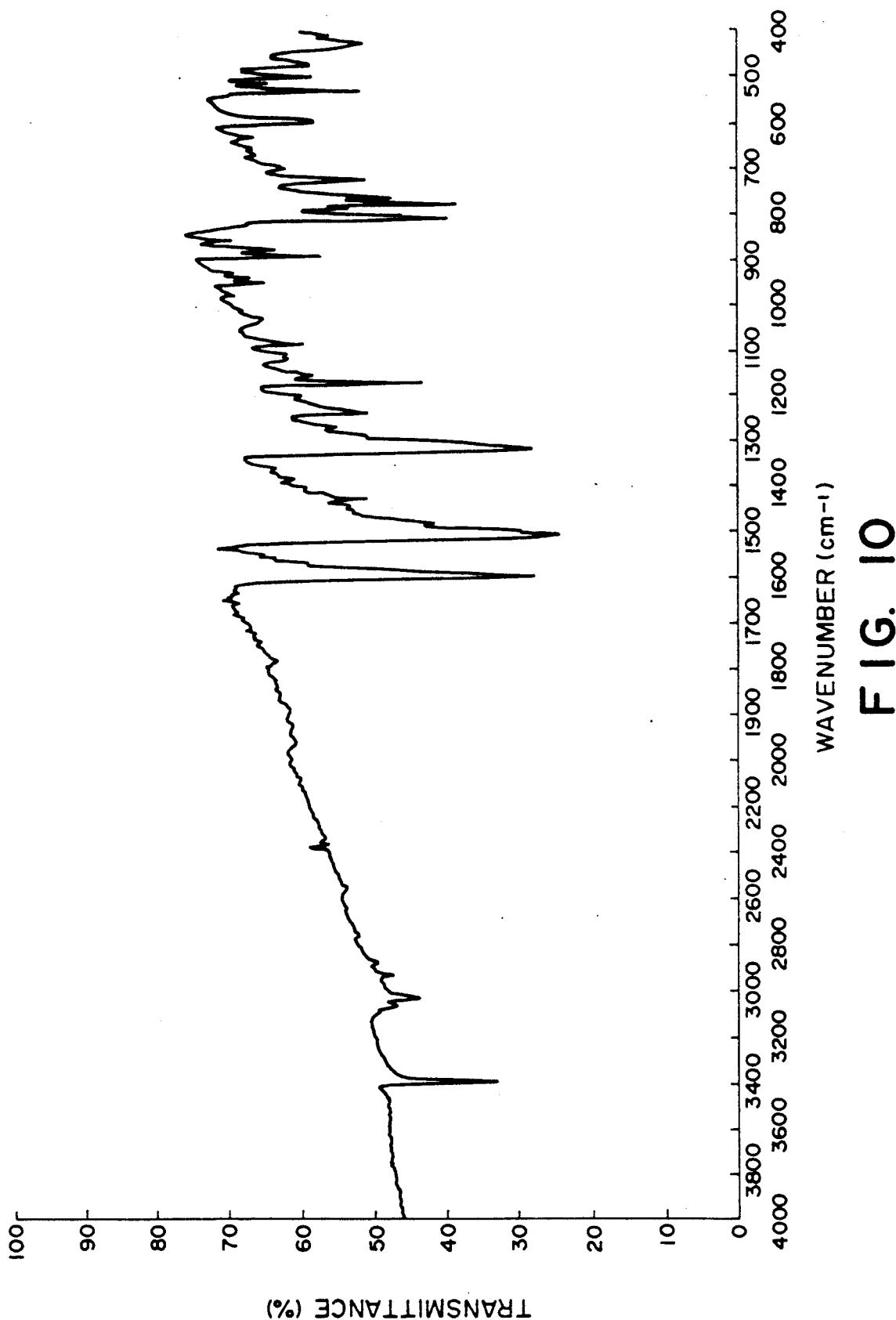

The infrared absorption spectrum (KBr tablet method) is shown in FIG. 10.

5.0 g (13.0 m moles) of the thus obtained 5-[4-(p-tolylamino)benzylidene]-5H-dibenzo[a,d]cycloheptene was added to 15 ml of N,N-dimethyl formamide, and 0.63 g (about 15.8 m moles) of oily sodium hydride (about 60%) was slowly added thereto at room temperature. After the addition, the mixture as such was stirred at room temperature for 15 minutes, and then 3.34 g (19.5 m moles) of benzyl bromide was added thereto. The reaction was subjected to reaction at 80° C. for 3 hours. After being left for cooling, the reaction mixture was poured into 130 ml of water and extracted with ethyl acetate. The organic layer was dried over anhydrous sodium sulfate, and then the solvent was removed under reduced pressure. The residue was separated and purified by use of a silica gel column, whereby 5.10 g of 5-[4-(N-benzyl-p-tolylamino)benzylidene-5H-dibenzo[a,d]cycloheptene was obtained (yield: 82.5%). The melting point was 59.0°–60.0° C. Elemental analysis as $C_{36}H_{29}N$ was as follows:

|  | C % | H % | N % |
|---|---|---|---|
| Calculated | 90.91 | 6.15 | 2.94 |
| Found | 90.87 | 6.18 | 2.95 |

Figure 11:
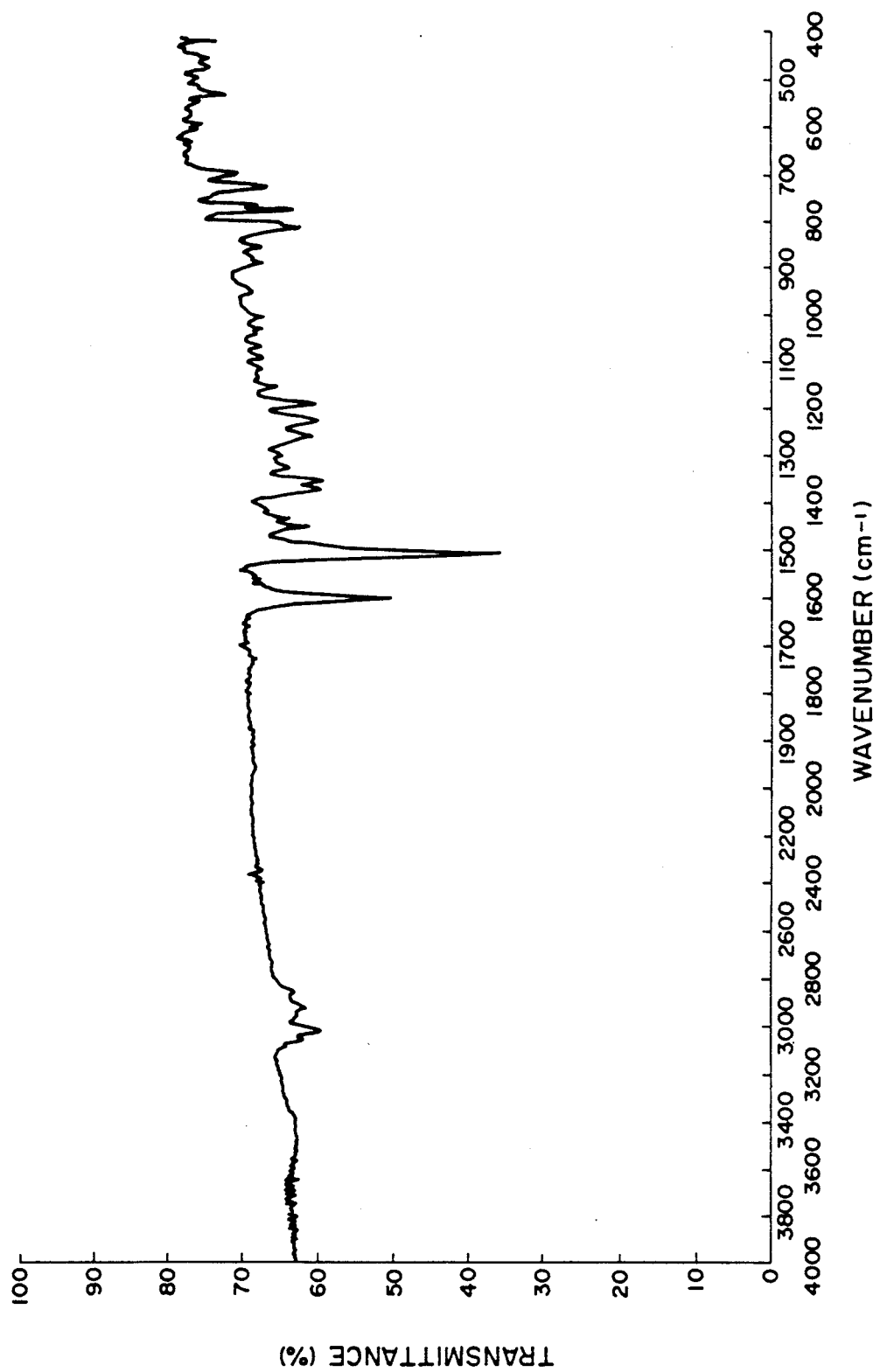

The infrared absorption spectrum (KBr tablet method) is shown in FIG. 11.

EXAMPLE 7

Synthesis of Exemplified Compound (51)

5.0 g (13.0 m mole) of 5-[4-(p-tolylamino)benzylidene]-5H-dibenzo[a,d]cycloheptene obtained in the same manner as in Example 6, 10.6 g (52.0 m moles) of iodobenzene, 3.05 g (22.1 m mole) of anhydrous potassium carbonate, and 0.60 g of copper powder were stirred and refluxed over an oil bath for 5 hours. After the end of reaction, the reaction mixture was filtered by suction, and the filtrate was washed successively with an aqueous 3–5% sodium thiosulfate solution and an aqueous NaCl solution. The organic layer was dried over anhydrous sodium sulfate and the solvent was removed therefrom under reduced pressure. The residue was separated and purified by use of a silica gel column, whereby 4.62 g of 5-[4-(N-phenyl-p- tolylamino)benzylidene]-5H-dibenzo[a,d]cycloheptene was obtained (yield: 77.0%). The melting point was 52.0°–53.0° C. Elemental analysis as $C_{35}H_{27}N$ was as follows:

|  | C % | H % | N % |
|---|---|---|---|
| Calculated | 91.07 | 5.90 | 3.03 |
| Found | 91.11 | 5.87 | 3.02 |

Figure 12:
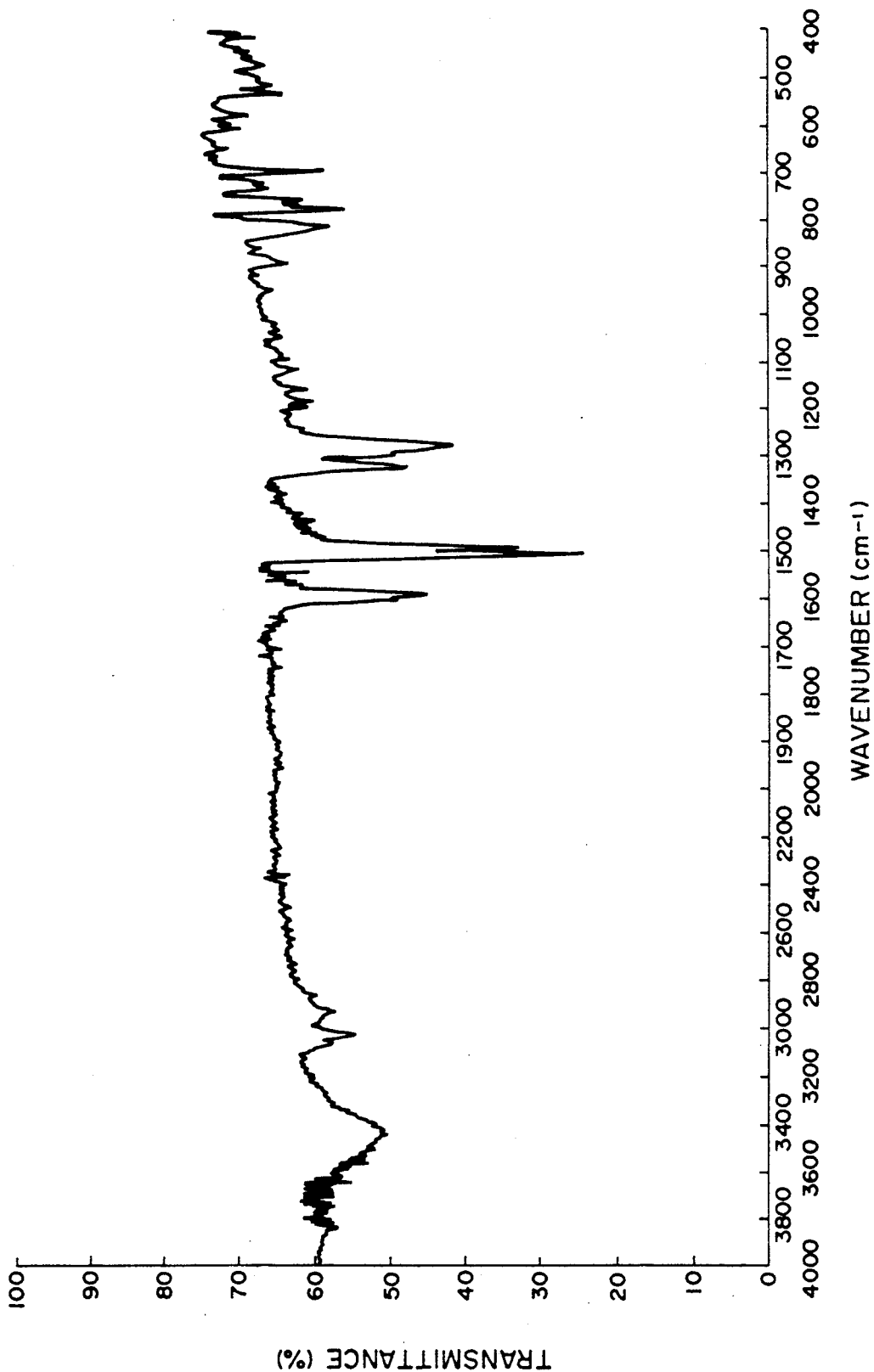

The infrared absorption spectrum (KBr tablet method) is shown in FIG. 12.

EXAMPLE 8

Synthesis of Exemplified Compound (32)

5.0 g (14.8 m moles) of 5-(4-acetylaminobenzylidene)-5H-dibenzo[a,d]cycloheptene obtained in the same manner as in Example 6 was added to 15 ml of N,N-dimethyl formamide, and 0.64 g (about 16 m moles) of oily sodium hydride (about 60%) was further added thereto at room temperature. Then, the mixture was stirred at room temperature for 15 minutes, and 1.82 g (16.0 m moles) of 2-chloropyridine was added thereto. The mixture as such was stirred at room temperature for 30 minutes, and then further stirred with heating at 100° C. for 2 hours. After being left for cooling, the reaction mixture was poured into 100 ml of water, and the precipitated crystal was recovered therefrom by filtration, dissolved into 30 ml of tetrahydrofuran. Then, the mixture was admixed with 0.84 g (15.5 m moles) of sodium methylate at room temperature and stirred as such at room temperature for one hour. The reaction mixture was poured into 100 ml of water, and the precipitated crystal was recovered therefrom by filtration, and recrystallized from ethanol, whereby 3.8 g of 5-[4-(2'-pyridylamino)benzylidene]-5H-dibenzo[a,d]cycloheptene was obtained (yield: 79.2%).

Then, 3.0 g (8.1 m mole) of the thus obtained 5-[4-(2'-pyridylamino)benzylidene]-5H-dibenzo[a,d]cycloheptene was added to 15 ml of tetrahydrofuran, and 0.35 g (about 8.8 m moles) of oily sodium hydride (about 60%) was slowly added thereto at room temperature. The mixture as such was stirred at room temperature for 15 minutes, and then 1.85 g (11.9 m moles) of ethyl iodine was added thereto. The mixture was refluxed with stirring for 3 hours. After being left for cooling, the reaction mixture was poured into 100 ml of water, and the precipitated crystal was recovered therefrom by filtration and recrystallized from methanol-acetone solvent mixture, whereby 1.92 g of 5-[4-(N-ethyl-2'-pyridylamino)benzylidene]-5H-dibenzo[a,d]cycloheptene was obtained (yield: 59.2%).

Elemental analysis as $C_{29}H_{24}N_2$ was as follows:

|  | C % | H % | N % |
|---|---|---|---|
| Calculated | 86.97 | 6.04 | 6.99 |
| Found | 86.94 | 6.01 | 7.05 |

EXAMPLE 9

Synthesis of Exemplified Compound (53)

8.91 g of 5-[4-(di-o-tolylamino)benzylidene]-5H-dibenzo[a,d]cycloheptene was obtained by synthesis in the same manner and quantitative relations as in Example 1, using diethyl-2-nitrobenzyl phosphonate synthesized from 2-nitrobenzylbromide and triethyl phosphite in place of diethyl-4-nitrobenzyl phosphonate of Example 1. The yield was 70.2%. The melting point was 153.0°–154.0° C. Elemental analysis as $C_{36}H_{29}N$ was as follows:

|  | C % | H % | N % |
|---|---|---|---|
| Calculated | 90.90 | 6.15 | 2.95 |
| Found | 90.86 | 6.17 | 2.97 |

Figure 13:
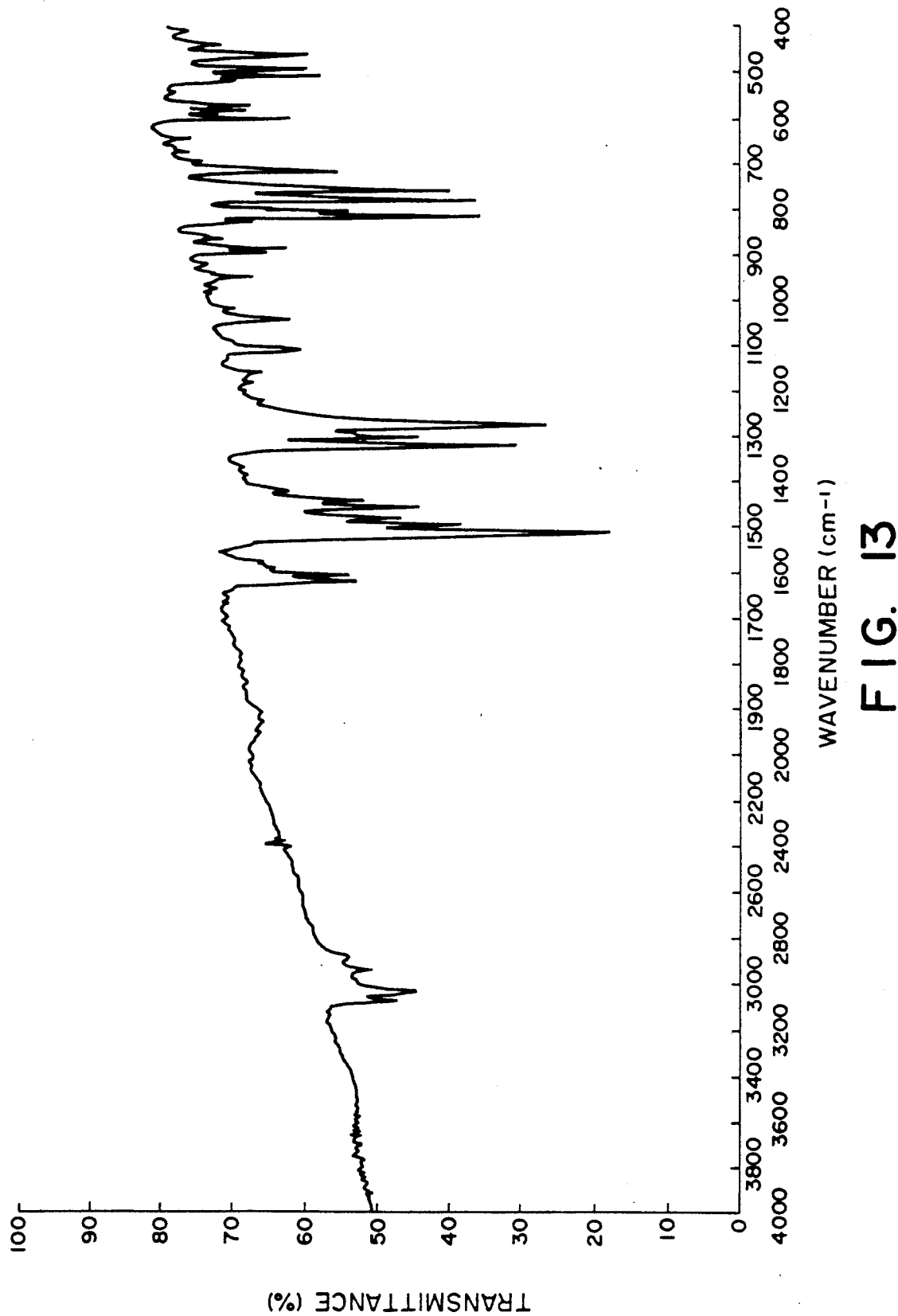

The infrared absorption spectrum (KBr tablet method) is shown in FIG. 13.

EXAMPLE 10

7 g of a pigment obtained by refluxing β-type copper phthalocyanin (Lionol Blue NCB toner, tradename of a product made by Toyo Ink Seizo K.K., Japan) successively in water, ethanol and benzene, followed by purification through filtration, 14 g of polyester adhesive 49,000 (solid content: 20%, trade name of a product made by Du Pont, USA), 35 g of toluene and 35 g of dioxane were mixed together and dispersed in a ball mill for 6 hours to prepare a coating solution. The coating solution was applied to an aluminum sheet to a film thickness of 0.5 μm as dried by means of a Meyer bar to prepare a charge generation layer.

Then, a solution prepared by dissolving 7 g of said exemplified compound (12) as a charge transport material and 7 g of polycarbonate resin (Panlite K-1300, trade name of a product made by Teijin Kasei K.K., Japan) in a solvent mixture composed of 35 g tetrahydrofuran and 35 g of chlorobenzene with stirring was applied onto the charge generation layer to a film thickness of 11 μm as dried by means of a Meyer whereby an electrophotographic photosensitive member having a photosensitive layer in a double layer structure was prepared.

The thus prepared electrophotographic photosensitive member was corona charged at −5KV according to a static system in an electrostatic copying paper test apparatus, Model-Sp-428, made by Kawaguchi Denki K.K., Japan, retained in a dark place for one second and exposed to light with an illuminance of 25 lux to investigate charging characteristics.

As the charging characteristics, a surface potential ($V_0$), a potential ($V_1$) dark attenuated for one second, and a light exposure quantity ($E\frac{1}{2}$) necessary for attenuating $V_1$ to one-half were measured.

Furthermore, in order to determine fluctuations in the light portion potential and the dark portion potential when repeatedly used, the photosensitive member prepared in this Example was pasted onto a cylinder for photosensitive drum of PPC copying machine NP-150Z made by Canon K.K., and was subjected to copying of 50,000 sheets by the copying machine. Fluctuations in the light portion potential ($V_L$) and the dark portion potential ($V_D$) at the initial and after the copying of 50,000 sheets were measured. The results are given in the following Table 1.

TABLE 1

|  | $V_0$ (V) | $V_1$ (V) | $E\frac{1}{2}$ (lux.sec) | Initial (V) |  | After copying of 50,000 sheets (V) |
|---|---|---|---|---|---|---|
| Example 1 | 697 | 688 | 1.2 | $V_D$ | 698 | 703 |
|  |  |  |  | $V_L$ | 78 | 98 |

EXAMPLES 11 TO 25 AND COMPARATIVE following structural formula was used as the charge generating material.

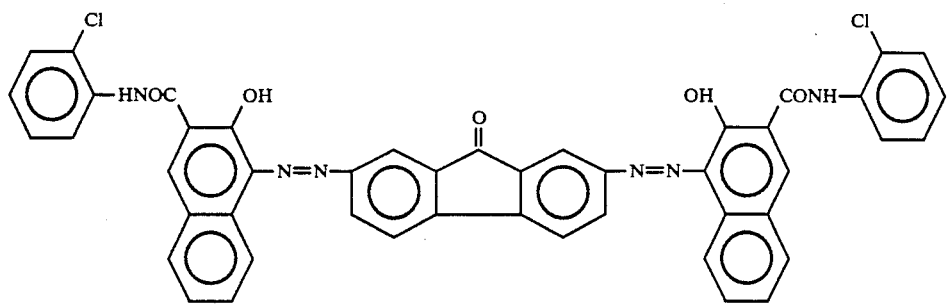

EXAMPLES 1 to 5

In the present Examples, electrophotographic photosensitive members were prepared in the same manner as in Example 10, except that the exemplified compounds (1), (4), (5), (7), (11), (13), (16), (17), (18), (31), (38), (39), (41), (45), and (48) were individually used as charge transport materials in place of the exemplified compound (12) of Example 10 and a pigment having the following structural formula was used as the charge generating material.

Electrophotographic characteristics of the respective photosensitive members were determined in the same manner as in Example 10. The results are shown below.

For comparison, electrophotographic photosensitive members were prepared in the same manner as above, using compounds of the following structural formulae as charge transport materials, and their electrophotographic characteristics were determined.

| | Comparative Compounds | |
|---|---|---|
| 1. | [structure] | British Patent 2,121,789 [=Japanese Patent Application Kokai (Laid-open) No. 198043/1983] |
| 2. | [structure] | The same as above |
| 3. | [structure] | U.S. Pat. No. 4,245,021 [=Japanese Patent Application Kokai (Laid-open) No. 110837/1979] |
| 4. | [structure] | Japanese Patent Application Kokai (Laid-open) No. 161247/1980] |

-continued

| Comparative Compounds | |
|---|---|
| 5. 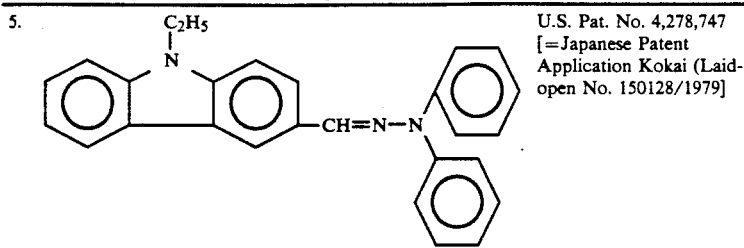 | U.S. Pat. No. 4,278,747 [=Japanese Patent Application Kokai (Laid-open No. 150128/1979] |

| Ex. No. | Exemplified Compound | $E_{\frac{1}{2}}$ (lux.sec) | $V_0$ (−Volt) | $V_1$ (−Volt) |
|---|---|---|---|---|
| 11 | (1) | 1.8 | 698 | 689 |
| 12 | (4) | 1.8 | 699 | 691 |
| 13 | (5) | 1.7 | 693 | 685 |
| 14 | (7) | 1.7 | 695 | 684 |
| 15 | (11) | 0.9 | 697 | 692 |
| 16 | (13) | 1.0 | 699 | 690 |
| 17 | (16) | 1.1 | 698 | 683 |
| 18 | (17) | 1.1 | 693 | 680 |
| 19 | (18) | 1.0 | 694 | 683 |
| 20 | (31) | 2.0 | 694 | 685 |
| 21 | (38) | 1.2 | 694 | 685 |
| 22 | (39) | 1.0 | 699 | 688 |
| 23 | (41) | 0.9 | 698 | 685 |
| 24 | (45) | 1.2 | 694 | 688 |
| 25 | (48) | 2.2 | 693 | 685 |

| Comp. Ex. | Comp. Compound | $E_{\frac{1}{2}}$ | $V_0$ | $V_1$ |
|---|---|---|---|---|
| 1 | 1 | 3.5 | 695 | 685 |
| 2 | 2 | 1.6 | 697 | 690 |
| 3 | 3 | 4.5 | 700 | 692 |
| 4 | 4 | 7.0 | 692 | 680 |
| 5 | 5 | 2.3 | 698 | 689 |

| | Initial | | After copying of 50,000 sheets | |
|---|---|---|---|---|
| Ex. No. | $V_D$(−Volt) | $V_L$(−Volt) | $V_D$(−Volt) | $V_L$(−Volt) |
| 11 | 698 | 105 | 678 | 159 |
| 12 | 699 | 110 | 680 | 161 |
| 13 | 694 | 108 | 672 | 153 |
| 14 | 696 | 107 | 675 | 160 |
| 15 | 697 | 69 | 689 | 89 |
| 16 | 699 | 70 | 690 | 84 |
| 17 | 699 | 72 | 689 | 90 |
| 18 | 693 | 71 | 702 | 91 |
| 19 | 694 | 79 | 684 | 99 |
| 20 | 693 | 117 | 674 | 157 |
| 21 | 694 | 68 | 685 | 79 |
| 22 | 698 | 69 | 690 | 80 |
| 23 | 698 | 70 | 689 | 83 |
| 24 | 694 | 72 | 693 | 86 |
| 25 | 693 | 108 | 671 | 152 |

| | Initial | | After copying of 50,000 sheets | |
|---|---|---|---|---|
| Com. Ex. | $V_D$ | $V_L$ | $V_D$ | $V_L$ |
| 1 | 698 | 190 | 648 | 283 |
| 2 | 699 | 90 | 653 | 235 |
| 3 | 702 | 225 | 645 | 366 |
| 4 | 692 | 273 | 626 | 405 |
| 5 | 697 | 145 | 637 | 277 |

It is obvious from the foregoing results that the present compounds have a better sensitivity than those of comparative compounds, and particularly considerably less fluctuations in potential by repeated charging and light exposure, and thus have a good stability.

EXAMPLE 26

An aqueous ammonia solution of casein (casein: 11.2 g, 28% aqua ammonia: 1 g, and water: 222 ml) was applied onto an aluminum cylinder by dip coating and dried to form a primer layer in a coating amount of 1.0 g/m².

Then, one part by weight of a charge generating material having the following structural formula, one part by weight of butyral resin (S-LEC BM-2, trade name of a product made by Sekisui Kagaku Kogyo K.K., Japan), and 30 parts by weight of isopropyl alcohol were dispersed in a ball mill disperse for 4 hours.

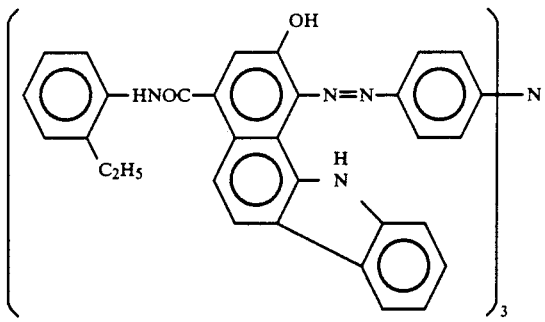

The resulting dispersion was applied onto the previously formed primer layer by dip coating and dried, whereby a charge generation layer having a film thickness of 0.3 μm was formed.

Then, one part by weight of the said exemplified charge transport material No. (14), one part by weight of polysulfone resin (P1700, trade name of a product made by Union Carbide, USA), and 6 parts by weight of monochlorobenzene were mixed together and made into solution with stirring by a stirrer. The resulting solution was applied onto the charge generation layer by dip coating and dried, whereby a charge transport layer having a film thickness of 12 μm was formed.

The thus prepared photosensitive member was corona charged at −5KV to measure the surface potential (initial volta $V_0$). Furthermore, the photosensitive member was left standing in a dark place for 5 seconds to measure the surface potential ($V_K$). The sensitivity was determined by measuring the necessary light exposure quantity ($E_{\frac{1}{2}}$ μJ/cm$^2$) for attenuating the potential $V_K$ after the dark attenuation to one-half, where a ternary semiconductor laser gallium/aluminium/arsenic (output power: 5 mW; oscillation wavelength: 780 nm) was used as a light source. The results are as follows:
$V_0$: −697 volts
Potential retention ($V_K/V_0 \times 100$): 97%
$E_{\frac{1}{2}}$: 1.2 μJ/cm$^2$ The photosensitive member was set in a laser beam printer (LBP-CX, trade name of a product made by Canon K.K., Japan) as an electrophotographic printer of reversal development type provided with the said semiconductor laser and subjected to an actual image-forming test under the following conditions:
Surface potential after primary charging: −700V
Surface potential after image light exposure: −150V (light exposure quantity: 2.0 μJ/cm$^2$)
Transfer potential: +700V
Developer polarity: negative polarity
Process speed: 50 mm/sec.
Developing condition (developing bias): −450V
Image light exposure scanning type: image scanning
Light exposure before primary charging: red entire surface light exposure at 50 lux.sec.

Image formation was carried out with a laser beam through line scanning according to letter signals and an image signals. A good print was obtained with respect to both letters and images.

EXAMPLE 27

3 g of 4-(4-dimethylaluminophenyl)-2,6-diphenyl-thiapyrylium perchlorate and 5 g of said exemplified charge transport compound (12) were mixed with 100 ml of a solution of polyester (Polyester Adhesive 49000, trade name of a product made by DuPont, USA) in toluene(50)-dioxane(50), and made into dispersion in a ball mill for 6 hours. The dispersion was applied to an aluminum sheet to a film thickness of 15 μm by a Meyer bar.

Electrophotographic characteristics of the thus prepared photosensitive member were determined in the same manner as in Example 10. The results are given below:
$V_0$: −698 volts
$V_1$: −695 volts
$E_{\frac{1}{2}}$: 1.8 lux.sec Initial $V_D$: −697 volts
$V_L$: −108 volts After copying of 50,000 sheets $V_D$: −676 volts
$V_L$: −150 volts

EXAMPLE 28

An aqueous ammonia solution of casein (casein: 11.2 g, 28% aqua ammonia: 1 g, and water: 222 ml) was applied to an aluminum plate and dried, whereby an adhesive layer having a film thickness of 1 μm was formed.

5 g of a disazo pigment having the following structural formula and a solution containing 2 g of butyral resin (butyralation degree: 63% by mole) in 95 ml of ethanol were made into dispersion, and the resulting dispersion was applied onto the adhesive layer and dried, whereby a charge generation layer having a film thickness of 0.4 μm was formed.

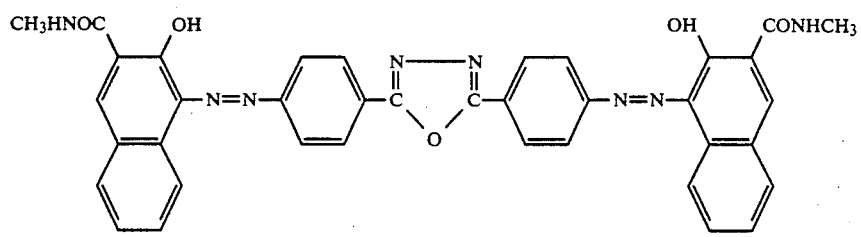

Then, a solution containing 5 g of said exemplified charge transport compound (14) and 5 g of poly-4,4'-dioxydiphenyl-2,2-propanecarbonate (viscosity average molecular weight: 30,000) in 150 ml of dichlomethane was applied onto the charge generation layer and dried, whereby a charge transport layer having a film thickness of 11 μm was formed. That is, an electrophotographic photosensitive member was prepared thereby.

Electrophotographic characteristics of the thus prepared electrophotographic photosensitive member were determined in the same manner as in Example 10. The results are given below:
$V_0$: −698 volts
$V_1$: −695 volts
$V_{\frac{1}{2}}$: 1.0 lux.sec Initial $V_D$: −695 volts
$V_L$: −72 volts After copying 50,000 sheets $V_D$: −683 volts
$V_L$: −83 volts

EXAMPLE 29

A molybdenum plate (substrate) having a thickness of 0.2 mm, whose surfaces were cleaned, was set at the predetermined position in a glow discharge vapor deposition vessel. Then, the vessel was evacuated to a vacuum of about $5 \times 10^{-6}$ Torr. Then, the input voltage to a heater was increased to stabilize the molybdenum substrate temperature at 150° C. Then, a hydrogen gas and a silane gas (15% by volume on the basis of the hydrogen gas) were introduced into the vessel, and the vessel vacuum was stabilized to 0.5 Torr by adjusting the gas flow rates and the main value to the vessels. A high frequency power of 5 MHz was put to an induction coil to generate glow discharge within the coil in the vessel, and an input power was set to 30 W.

An amorphous silicon film was made to grow on the substrate under these conditions and kept under the same conditions until the film thickness was 2 μm.

Then, the glow discharge was discontinued. Then, the heater and the high frequency power source were turned off, and after the substrate temperature reached 100° C., the inflow valves of hydrogen gas and silane gas were closed. After the vessel was made less than $10^{-5}$ Torr, the vessel was returned to the atmospheric pressure, and the substrate was taken out of the vessel. Then, a charge transport layer was formed on the amorphous silicon layer in the same manner as in Example 10.

The thus obtained photosensitive member was set in a charge-light exposure test apparatus and corona charged at ⊖6KV and immediately exposed to a light image. The light image was irradiated onto the photosensitive member through a transmission-type test chart, using a tungsten lamp light source. Immediately thereafter, a good toner image was obtained on the surface of photosensitive member by cascading a ⊕ chargeable developer (containing both toners and carriers) over the surface of photosensitive member.

EXAMPLE 30

3 g of 4-(4-dimethylaminophenyl)-2,6-diphenyl-thiapyrylium perchlorate and 3 g of poly (4,4'-isopropylidenediphenylenecarbonate) were thoroughly dissolved in 200 ml of dichloromethane, and then 100 ml of toluene was added thereto precipitate eutectic complexes. The precipitate was recovered therefrom by filtration and admixed with dichloromethane to redissolve the precipitate. Then, 100 ml of n hexane was added to the solution to obtain a precipitate of eutectic complexes.

5 g of the eutectic complexes was added to 95 ml of a methanol solution containing 2 g of polyvinylbutyral and made into dispersion in a ball mill for 6 hours. Then the dispersion was applied to an aluminum plate having a casein layer by a Meyer bar to a film thickness of 0.4 μm, as dried, to form a charge generation layer.

Then, a charge transport layer as a covering layer was formed on the charge generation layer in the same manner as in Example 10, except that the exemplified compound (37) was used as a charge transport material.

Electrophotographic characteristics of the thus prepared photosensitive member were determined in the same manner as in Example 10. The results are given below:

$V_0$: $-700$ volts
$V_1$: $-692$ volts
$E_{\frac{1}{2}}$: 1.1 lux.sec

Initial $V_D$: $-692$ volts
$V_L$: $-67$ volts

After copying 50,000 sheets $V_D$: $-690$ volts
$V_L$: $-82$ volts

EXAMPLE 31

5 g of the same eutectic complexes as in Example 30 and 5 g of said exemplified charge transport compound (40) were added to 150 ml of a tetrahydrofuran solution of polyester (Polyester Adhesive 49000: trade name of a product made by Du Pont, USA), and thoroughly mixed with stirring. The resulting mixture was applied to an aluminum sheet by a Meyer bar to a film thickness of 15 μm, as dried.

Electrophotographic characteristics of the thus prepared photosensitive member were measured in the same manner as in Example 10.

The results are shown below:

$V_0$: $-698$ volts
$V_1$: $-695$ volts
$E_{\frac{1}{2}}$: 1.1 lux.sec

Initial $V_D$: $-695$ volts
$V_L$: $-69$ volts

After copying of 50,000 sheets $V_D$: $-689$ volts
$V_L$: $-88$ volts

What we claim is:

1. An electrophotographic photosensitive member, which comprises photosensitive layer containing a compound represented by the following general formula [I]:

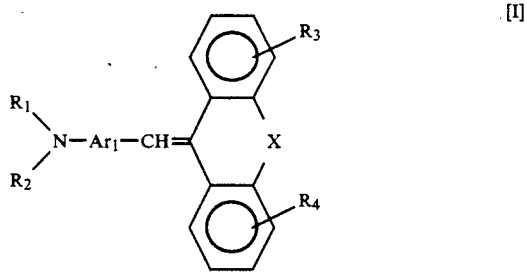

wherein X is —CH$_2$CH$_2$— or —CH=CH—; R$_1$ and R$_2$ are alkyl groups, aralkyl groups, aromatic groups or heterocyclic groups; R$_3$ and R$_4$ are hydrogen atoms, alkyl groups, alkoxy groups or halogen atoms; and Ar$_1$ is an aromatic group or a heterocyclic group.

2. An electrophotographic photosensitive member according to claim 1, wherein the compound represented by the general formula [I] is a compound represented by the following general formula [II]:

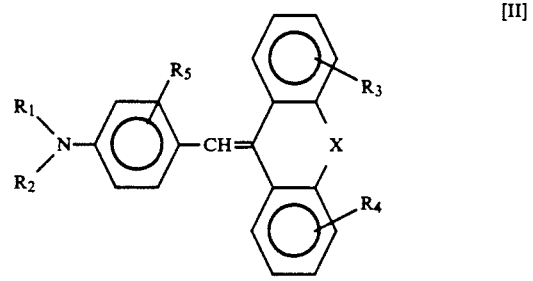

wherein X, R$_1$, R$_2$, R$_3$ and R$_4$ have the same meanings as defined above and R$_5$ is a hydrogen atom, an alkyl group, an alkoxy group, a halogen atom or a nitro group.

3. An electrophotographic photosensitive member according to claim 1, wherein the compound represented by the general formula [I] is a compound represented by the following general formula [III]:

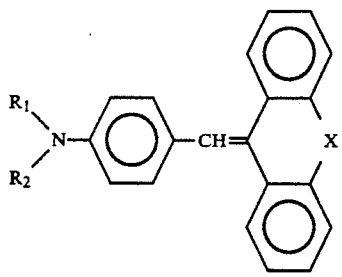

wherein X is —CH$_2$CH$_2$— or —CH=CH—, and R$_1$ and R$_2$ are aromatic groups.

4. An electrophotographic photosensitive member according to claim 1, 2 or 3, wherein photosensitive layer containing the compound is a charge transport layer in a photosensitive layer of double layer structure composed of a charge generation layer and a charge transport layer.

5. An electrophotographic photosensitive member according to claim 1, 2, or 3, wherein photosensitive layer containing the compound is a charge transport layer in a photosensitive layer of double layer structure composed of a charge generation layer and a charge transport layer, and the charge generation layer contains an azo pigment represented by the following general formula:

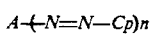

wherein A is a central skeleton, Cp is a coupler portion, and n is an integer of 2 or 3.

6. An electrophotographic photosensitive member according to claim 2, wherein R$_1$ and R$_2$ are groups selected from

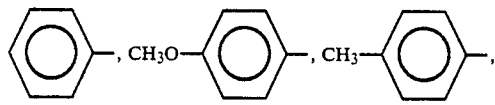

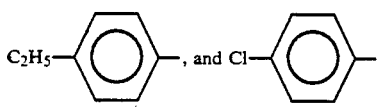

in the compound represented by the general formula [II].

7. An electrophotographic photosensitive member according to claim 3, wherein R$_1$ and R$_2$ are groups selected from

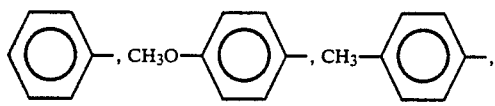

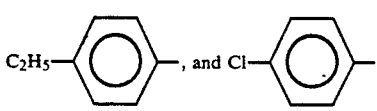

in the compound represented by the general formula [III].

8. An electrophotographic photosensitive member according to claim 2, wherein R$_1$ and R$_2$ are groups selected from CH$_3$—, C$_2$H$_5$—,

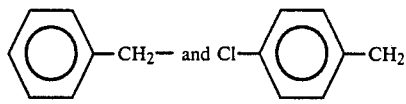

in the compound represented by the general formula [II].

9. A 5H-dibenzo[a,d]cycloheptanylidene derivative and a 5H-dibenzo[a,d]cycloheptenylidene derivative represented by the following general formula [I]:

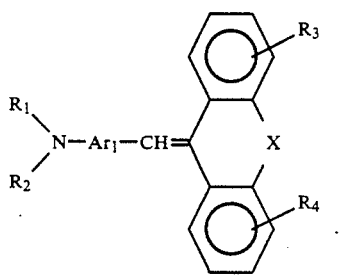

wherein X is —CH$_2$—CH$_2$— or —CH=CH—; R$_1$ and R$_2$ are alkyl groups, aralkyl groups, aromatic groups or heterocyclic groups; R$_3$ and R$_4$ are hydrogen atoms, alkyl groups, alkoxy groups or halogen atoms; and Ar$_1$ is an aromatic group or a heterocyclic group.

10. A 5H-dibenzo[a,d]cycloheptanylidene derivative and a 5H-dibenzo[a,d]cycloheptenylidene derivative according to claim 9, wherein the compounds represented by the general formula [I] are compounds represented by the following general formula [II]:

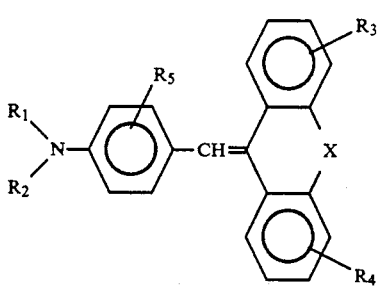

wherein X, R$_1$, R$_2$, R$_3$ and R$_4$ have the same meanings as defined above, and R$_5$ is a hydrogen atom, an alkyl group, an alkoxy group, a halogen atom or a nitro group.

11. A 5H-dibenzo[a,d]cycloheptanylidene derivative and a 5H-dibenzo[a,d]cycloheptenylidene derivative according to claim 9, wherein the compounds represented by the general formula [I] are compounds represented by the following general formula [III]:

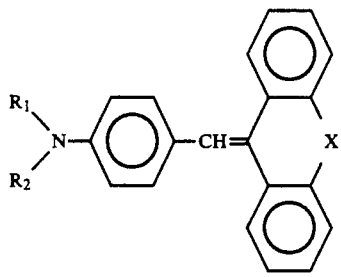

wherein X is —$CH_2$—$CH_2$— or —CH=CH—, and $R_1$ and $R_2$ are aromatic groups.

12. A 5H-dibenzo[a,d]cycloheptanylidene derivative and a 5H-dibenzo[a,d]cycloheptenylidene derivative according to claim 10, wherein $R_1$ and $R_2$ are groups selected from $CH_3$—, $C_2H_5$—,

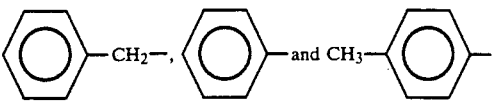

in the compounds represented by the general formula [II].

13. A 5H-dibenzo[a,d]cycloheptanylidene derivative and a 5H-dibenzo[a,d]cycloheptenylidene derivative according to claim 10, wherein $R_1$ and $R_2$ are groups selected from $CH_3$—, $C_2H_5$—,

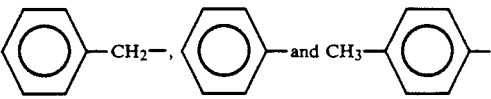

in the compounds represented by the general formula [II].

* * * * *

UNITED STATES PATENT AND TRADEMARK OFFICE
CERTIFICATE OF CORRECTION

PATENT NO. : 5,024,912
DATED : June 18, 1991
INVENTOR(S) : TOSHIE NEISHI, ET AL.

Page 1 of 2

It is certified that error appears in the above-identified patent and that said Letters Patent is hereby corrected as shown below:

On the Title page:

IN [56] REFERENCES CITED

Under Primary Examiner: "Girard L. Raymond" should read --Richard L. Raymond--.

IN [57] ABSTRACT

Line 2, "[1,d]" should read --[a,d]--.

COLUMN 15

In Formula (43), "$/CH_3$" should be deleted.

COLUMN 27

Line 36, "printers" should read --printers,--.

COLUMN 34

Line 1, "The-yield" should read --The yield--.
Line 34, "Meyer" should read --Meyer bar,--.

COLUMN 41

Line 30, "n hexane" should read --n-hexane--.

COLUMN 42

Line 20, "comprises" should read --comprises a--.

UNITED STATES PATENT AND TRADEMARK OFFICE
CERTIFICATE OF CORRECTION

PATENT NO. : 5,024,912
DATED : June 18, 1991
INVENTOR(S) : TOSHIE NEISHI, ET AL.

It is certified that error appears in the above-identified patent and that said Letters Patent is hereby corrected as shown below:

COLUMN 43

Line 17, "wherein" should read --wherein the--.
Line 23, "wherein" should read --wherein the--.

Line 68, "$C_2H_5-$," should read --$C_2H_5-$, $CH_3O-$,--.

Signed and Sealed this

Eighteenth Day of May, 1993

Attest:

MICHAEL K. KIRK

Attesting Officer     Acting Commissioner of Patents and Trademarks